US009125419B2

(12) United States Patent
Asolkar et al.

(10) Patent No.: US 9,125,419 B2
(45) Date of Patent: Sep. 8, 2015

(54) *BACILLUS* SP. STRAIN WITH ANTIFUNGAL, ANTIBACTERIAL AND GROWTH PROMOTION ACTIVITY

(71) Applicant: Marrone Bio Innovations, Inc, Davis, CA (US)

(72) Inventors: Ratnakar Asolkar, Davis, CA (US); Ana-Lucia Cordova-Kreylos, Davis, CA (US); Christopher D McCort, Davis, CA (US); Debora Wilk, Woodland, CA (US); Carly Todd, Sacramento, CA (US); Hai Su, Woodland, CA (US); Pamela Marrone, Davis, CA (US)

(73) Assignee: Marrone Bio Innovations, Inc., Davis, CA (US)

( * ) Notice: Subject to any disclaimer, the term of this patent is extended or adjusted under 35 U.S.C. 154(b) by 0 days.

(21) Appl. No.: 13/835,677

(22) Filed: Mar. 15, 2013

(65) Prior Publication Data

US 2014/0128256 A1    May 8, 2014

Related U.S. Application Data

(60) Provisional application No. 61/683,174, filed on Aug. 14, 2012.

(51) Int. Cl.
  *A01N 63/02*    (2006.01)
  *C12N 1/20*     (2006.01)
  *C12R 1/07*     (2006.01)

(52) U.S. Cl.
  CPC  *A01N 63/02* (2013.01); *C12N 1/20* (2013.01); *C12R 1/07* (2013.01)

(58) Field of Classification Search
  None
  See application file for complete search history.

(56) References Cited

U.S. PATENT DOCUMENTS 6,096,306 A * 8/2000 Bravo et al. .............. 424/93.461

FOREIGN PATENT DOCUMENTS

WO    WO9628031    *  9/1996
WO    WO 2007095259 A2   8/2007

OTHER PUBLICATIONS

Chau et al. (Role of RecA in the Protection of DNA Damage by UV-A in *Escherichia coli*., Journal of Experimental Microbiology and Immunology (2008), vol. 12, pp. 39-44.*
C3CKA8_BACTU (last viewed on Nov. 25, 2014).*
Janousek et al., Control of brown rot and shot hole in almond: 2009 field trial, Department of Plant Pathology UC Davis (2010), pp. 1st-4$^{th}$.*
Arena, J. P. et al. "The mechanism of action of avermectins in *Caenorhabditis elegans*—correlation between activation of glutamate-sensitive chloride current, membrane binding and biological activity." *Journal of Parasitology* 81: 286-294(1995).
Thompson, G. D. et al. "Spinosad—a case study: an example from a natural products discovery programme." *Pest Management Science* 56: 696-702(2000).

(Continued)

*Primary Examiner* — Alexander Kim
(74) *Attorney, Agent, or Firm* — Ying-Horng Liu

(57) ABSTRACT

Disclosed herein is a *Bacillus* strain, *Bacillus* sp. isolate F727, that produces metabolites with pesticidal activities. Also provided are bioactive compositions and metabolites derived from cultures of *Bacillus* sp. isolate F727 capable of controlling pests; as well as methods of use of the strain and its metabolites for controlling pests.

11 Claims, 13 Drawing Sheets

(56) References Cited

OTHER PUBLICATIONS

Krieg, A. et al. "*Bacillus thuringiensis* var. tenebrionis: Ein neuer, gegenuber Larven von Coleopteren wirksamer Pathotyp." *Z. Angew. Entomol.* 96: 500-508(1983).

Asolkar, R. N. et al. Daryamides A-C, Weakly Cytotoxic Polyketides from a Marine-Derived Actinomycete of the Genus *Streptomyces* strain CNQ-085 *J. Nat. Prod.* 69:1756-1759 (2006).

WC James (1971) "A Manual of Assessment Keys in Plant Diseases." American Phytopathological Society. ISBN 978-0-89054-081-7.

* cited by examiner

Figure 17

BACILLUS SP. STRAIN WITH ANTIFUNGAL, ANTIBACTERIAL AND GROWTH PROMOTION ACTIVITY

CROSS-REFERENCE TO RELATED APPLICATIONS

This application claims the benefit of U.S. Provisional Patent Application No. 61/683,174 filed Aug. 14, 2012; the disclosure of which is hereby incorporated by reference in its entirety for all purposes.

SEQUENCE LISTING

The instant application contains a Sequence Listing which has been submitted in ASCII format via EFS-Web and is hereby incorporated by reference in its entirety. Said ASCII copy, is named MOI-42034-US-SEQ.txt and is 16 kB in size.

TECHNICAL FIELD

The present disclosure is in the field of biopesticticides and pest control; in particular microbial pesticides and the microbial strains that produce them.

BACKGROUND

Natural products are substances produced by microbes, plants, and other organisms. Microbial natural products offer an abundant source of chemical diversity, and there is a long history of utilizing natural products for pharmaceutical purposes. Despite the emphasis on natural products for human therapeutics, where more than 50% are derived from natural products, only 11% of pesticides are derived from natural sources. Nevertheless, natural product pesticides have a potential to play an important role in controlling pests in both conventional and organic farms. Secondary metabolites produced by microbes (bacteria, actinomycetes and fungi) provide novel chemical compounds which can be used either alone or in combination with known compounds to effectively control insect pests and to reduce the risk for resistance development. There are several well-known examples of microbial natural products that are successful as agricultural insecticides (Thompson et al., 2000; Arena et al., 1995; Krieg et al. 1983).

The development of a microbial pesticide starts with the isolation of a microbe in a pure culture. It then proceeds with efficacy and spectrum screening using in vitro, in vivo or pilot scale trials in a greenhouse and in the field. At the same time, active compounds produced by the microbe are isolated and identified. For the commercialization of a microbial pesticide, the microbe has to be economically produced by fermentation at an industrial scale and formulated with approved biocompatible additives to increase efficacy and to maximize the ease of application.

With the development of increasing resistance to chemical pesticides, the spectrum of available pesticides is narrowing. In addition, non-naturally-occurring pesticides can have detrimental environmental effects. Accordingly, there is a need for new, naturally-occurring pesticides to which plant pathogens have not developed resistance, and which have minimal environmental effects.

SUMMARY

Disclosed herein is a microbial strain, *Bacillus* sp. isolate F727, having pesticidal activity. This strain produces bioactive metabolites active in controlling pests and promoting plant growth. Also disclosed are methods for using *Bacillus* sp. isolate 727 and its metabolites for controlling pests and promoting plant growth. In a particular embodiment, the *Bacillus* sp. may have at least one of the identifying characteristics of NRRL B-50768.

Furthermore, the *Bacillus* sp. can have a 16S rRNA gene sequence with at least 99% identity and particularly 99.5% identity to the consensus sequence set forth in SEQ ID NO: 3 and comprising a forward sequence having at least 99% identity and particularly 995% identity to the sequence set forth in SEQ ID NO:1, and a reverse sequence having at least 99% identity and particularly 99.5% identity to the sequence set forth in SEQ ID NO:2.

Further provided is a substantially pure culture or whole cell broth comprising said strain, or cell fraction, extract, supernatant and/or substances or compounds derived from said strain or extract thereof.

Further provided is a method for modulating pest infestation in a plant comprising applying to the plant and/or seeds thereof and/or substrate used for growing said plant an amount of said *Bacillus* sp. isolate F727 (and/or a culture, cell fraction, extract, supernatant and/or substances or compounds derived from said strain or extract) that is effective to modulate said pest infestation. In a particular embodiment, the pest is a plant fungus such as *Botrytis, Sclerotinia, Rhizoctonia* or *Bipolaris*.

Also provided are methods for promoting plant growth and/or seed germination, wherein the methods comprise applying to the plant and/or seeds thereof and/or substrate used for growing said plant an amount of said *Bacillus* sp. isolate F727 (and/or a culture, cell fraction, extract, supernatant and/or substances or compounds derived from said strain or extract) that is effective to promote plant growth and/or seed germination.

In particular embodiments, said *Bacillus* produces a compound selected from the group consisting of:

(a) compound "A" that
  (i) may be obtainable from a *Bacillus* sp., particularly, *Bacillus* sp. isolate 727;
  (ii) has pesticidal activity;
  (iii) has a molecular weight of about 1020-1060 and more particularly, 1044 as determined by Liquid Chromatography/Mass Spectroscopy (LC/MS);
  (iv) has $^1$H NMR values of δ 7.15, 6.72, 4.81, 4.70, 4.65, 4.40, 4.35, 4.25, 4.15, 3.85, 3.65, 3.50, 3.22, 2.85, 2.80, 2.65, 2.45, 2.35, 2.30, 2.20, 1.95, 1.55, 1.31, 1.20 and 0.85;
  (v) has a High Pressure Liquid Chromatography (HPLC) retention time of about 6-12 minutes, more specifically about 8 minutes and even more specifically about 8.31 min on a reversed phase C-18 HPLC (Phenomenex, Luna 5μ C18(2) 100 A, 100×4.60 mm) column using a water:acetonitrile ($CH_3CN$) gradient solvent system (0-20 min; 90-0% aqueous $CH_3CN$, 20-24 min; 100% $CH_3CN$, 24-27 min; 0-90% aqueous $CH_3CN$, 27-30 min; 90% aqueous $CH_3CN$) at 0.5 mL/min flow rate and UV detection at 210 nm;
  (vi) optionally contains 47 carbons, 72 hydrogens, 12 nitrogens, and 15 oxygens; and
  (vii) is optionally a peptide and may comprise glutamine (1 unit), proline (1 unit), serine (1 unit), tyrosine (1 unit) and asparagine (3 units);

(b) Compound "B" that
(i) has pesticidal activity;
(ii) has a molecular weight of about 1030-1080 and more particularly, 1058 as determined by Liquid Chromatography/Mass Spectroscopy (LC/MS);
(iii) has an High Pressure Liquid Chromatography (HPLC) retention time of about 6-14 minutes, more specifically about 8 minutes and even more specifically about 8.67 min on a reversed phase C-18 HPLC column using a water:acetonitrile ($CH_3CN$) gradient solvent system (0-20 min; 90-0% aqueous $CH_3CN$, 20-24 min; 100% $CH_3CN$, 24-27 min; 0-90% aqueous $CH_3CN$, 27-30 min; 90% aqueous $CH_3CN$) at 0.5 mL/min flow rate and UV detection at 210 nm;
(iv) optionally comprises 48 carbons, 74 hydrogens, 12 nitrogens, and 15 oxygens; and
(v) is optionally a peptide and may comprise glutamine (1 unit), proline (1 unit), serine (1 unit), tyrosine (1 unit) and asparagine (3 units); and
(c) Compound "C" that
(i) has pesticidal activity;
(ii) has a molecular weight of about 1050-1120 and more particularly, 1072 as determined by Liquid Chromatography/Mass Spectroscopy (LC/MS);
(iii) has a High Pressure Liquid Chromatography (HPLC) retention time of about 6-14 minutes, more specifically about 9 minutes and even more specifically about 9.19 min on a reversed phase C-18 HPLC column using a water:acetonitrile ($CH_3CN$) gradient solvent system (0-20 min; 90-0% aqueous $CH_3CN$, 20-24 min; 100% $CH_3CN$, 24-27 min; 0-90% aqueous $CH_3CN$, 27-30 min; 90% aqueous $CH_3CN$) at 0.5 mL/min flow rate and UV detection at 210 nm;
(iv) optionally contains 49 carbons, 76 hydrogens, 12 nitrogens, and 15 oxygens; and
(v) is optionally a peptide and may comprise glutamine (1 unit), proline (1 unit), serine (1 unit), tyrosine (1 unit) and asparagine (3 units).

Also provided herein is a *Bacillus* strain having the following characteristics:
(a) at least one of:
(1) a nucleotide sequence having at least 99.5% identity to a 16SrRRNA sequence set forth in SEQ ID NO:3;
(2) a nucleotide sequence having at least 95% identity to a recA sequence set forth in SEQ ID NO:10 and
(3) a nucleotide sequence having at least 90% identity to a reverse phoR sequence set forth in SEQ ID NO:13;
(b) produces a compound that
(i) has pesticidal activity;
(ii) has a molecular weight of about 1020-1120 as determined by Liquid Chromatography/Mass Spectroscopy (LC/MS), and
(iii) has a High Pressure Liquid Chromatography (HPLC) retention time of about 6-15 minutes on a reversed phase C-18 HPLC column using a water:acetonitrile ($CH_3CN$) gradient solvent system (0-20 min; 90-0% aqueous $CH_3CN$, 20-24 min; 100% $CH_3CN$, 24-27 min; 0-90% aqueous $CH_3CN$, 27-30 min; 90% aqueous $CH_3CN$) at 0.5 mL/min flow rate and UV detection at 210 nm, and
(iv) is optionally a peptide;
(c) is resistant to Kanamycin, Chloramphenicol, Ampicillin, Penicillin, Cefuroxime, Piperacillin, Tetracycline; and
(d) possesses alkaline phosphatase, esterase, acid phosphatase, and naphthol-AS-BI-phosphohydrolase activity.

Also provided is a combination comprising said *Bacillus* sp. isolate F727, a substantially pure culture, cell fraction, extract, supernatant and substances, metabolites or compounds derived from said strain or extract thereof and at least one of (a) a second substance which may be a chemical or biological pesticide and (b) at least one of a carrier, diluent, surfactant, adjuvant. The combination may be a composition and may be coated onto a seed.

Further provided is a method for modulating pest infestation in a plant comprising applying to the plant and/or seeds thereof and/or substrate used for growing said plant an amount of said combination effective to modulate said pest infestation. In a particular embodiment, the pest is a plant fungus such as *Botrytis*, *Sclerotinia*, *Rhizoctonia* or *Bipolaris*.

Further provided is the use of a composition, optionally in combination with a second substance, to formulate a pesticidal composition, wherein the composition is selected from the group consisting of:
(a) a pure culture of the strain of claim 1,
(b) a cell fraction of the strain of claim 1,
(c) a supernatant derived from the strain of claim 1,
(d) an extract of any of (i), (ii) or (iii),
(d) a metabolite of the strain of claim 1,
(f) compound A,
(g) compound B, and
(h) compound C; and
the second substance is selected from the group consisting of:
(a) a pesticide,
(b) a plant growth-promoting agent,
(c) a carrier,
(d) an adjuvant,
(e) a surfactant,
(f) a fertilizer, and
(g) an anti-phytopathogenic agent.

In one aspect, the pesticide is selected from the group consisting of a bactericide, a fungicide and a nematicide.

BRIEF DESCRIPTION OF THE FIGURES

FIG. 17 shows effects of supernatants from F727 fermentation, and controls, on mycelial growth of *S. rolfsii* in an in vitro assay. Effects of water (DI water), unfiltered F727 supernatant (F727 unfiltered), filtered F727 supernatant (F727 filtered) and Pristine® are shown. For each test material and control, two volumes were evaluated: in each pair of bars, the leftmost bar shows results using 25 μl, and the rightmost bar shows the results using 50 μl.

DETAILED DESCRIPTION

Figure 1:
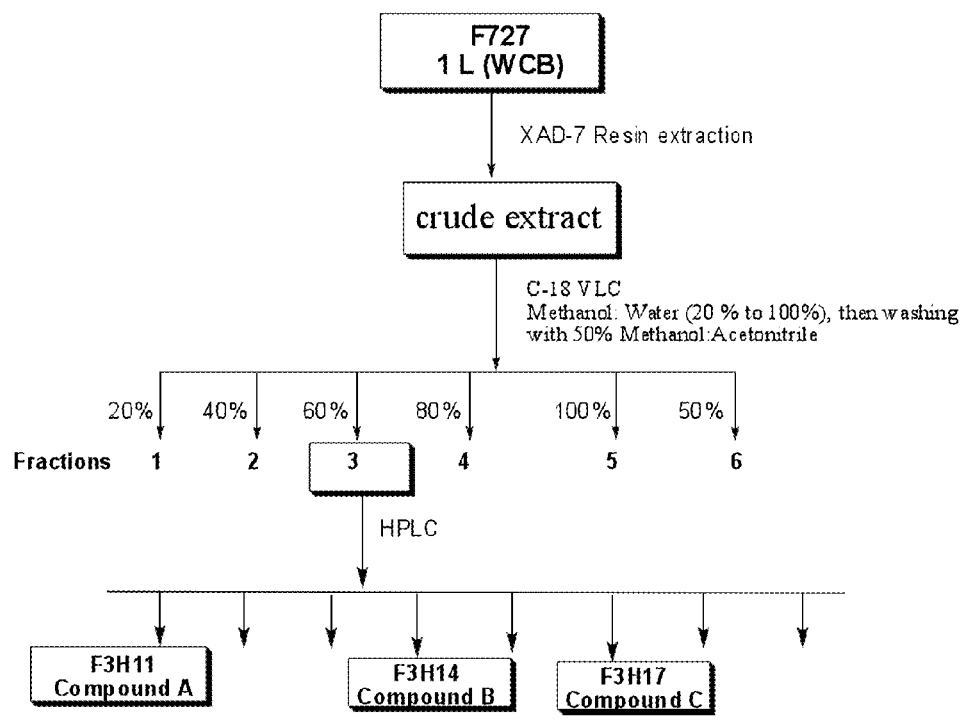
FIG. 1 shows a schematic representation of purification scheme for obtaining the compounds of the invention from culture broth.

While the compositions and methods disclosed herein are susceptible to various modifications and alternative forms, exemplary embodiments will herein be described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

Where a range of values is provided, it is understood that each intervening value, to the tenth of the unit of the lower limit unless the context clearly dictates otherwise, between the upper and lower limit of that range and any other stated or intervening value in that stated range, is included therein. Smaller ranges are also included. The upper and lower limits of these smaller ranges are also included therein, subject to any specifically excluded limit in the stated range.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

As defined herein, "derived from" means directly isolated or obtained from a particular source or alternatively having identifying characteristics of a substance or organism isolated or obtained from a particular source. In the event that the "source" is an organism, "derived from" means that it may be isolated or obtained from the organism itself or medium used to culture or grow said organism.

As defined herein, "whole broth culture" refers to a liquid culture containing both cells and media. If bacteria are grown on a plate the cells can be harvested in water or other liquid, to provide a whole broth culture.

The term "supernatant" refers to the liquid remaining when cells that are grown in broth or harvested in another liquid from an agar plate are removed by centrifugation, filtration, sedimentation, or other means well known in the art.

As defined herein, "filtrate" refers to liquid from a whole broth culture that has been passed through a membrane.

As defined herein, "extract" refers to liquid substance removed from cells by a solvent (water, detergent, buffer) and separated from the cells by centrifugation, filtration or other method.

As defined herein, "metabolite" refers to a compound, substance or byproduct of a fermentation of a microorganism, or supernatant, filtrate, or extract obtained from a microorganism that has pesticidal and particularly, bactericidal or fungicidal activity. As defined herein, an "isolated compound" is essentially free of other compounds or substances, e.g., at least about 20% pure, preferably at least about 40% pure, more preferably about 60% pure, even more preferably about 80% pure, most preferably about 90% pure, and even most preferably about 95% pure, as determined by analytical methods, including but not limited to chromatographic and electrophoretic methods. The terms "metabolite" and "compound" may be used interchangeably.

A "carrier" as defined herein is an inert, organic or inorganic material, with which the active ingredient is mixed or formulated to facilitate its application to a plant or other object to be treated, or to facilitate its storage, transport and/or handling.

The term "modulate" as defined herein is used to mean to alter the amount of pest infestation or rate of spread of pest infestation.

The term "pest infestation" as defined herein, is the presence of a pest in an amount that causes a harmful effect including a disease or infection in a host population or emergence of an undesired weed in a growth system.

A "pesticide" as defined herein, is a substance derived from a biological product or chemical substance that increase mortality or inhibits the growth rate of plant pests and includes but is not limited to nematicides, insecticides, plant fungicides, plant bactericides, and plant viricides.

Identification and Characterization of *Bacillus* sp. F727

*Bacillus* sp. isolate F727 was identified as a novel strain of *Bacillus* using a polyphasic approach combining 16S rRNA sequence determination, fatty acid analysis, MALDI-TOF protein analysis and characterization using several biochemical assays. See Examples 1-4, infra.

Metabolites produced by fermentation of *Bacillus* sp. F727 were isolated. See Example 5, infra. Certain of these metabolites demonstrated activity against fungal and bacterial pathogens both in vitro and in vivo. See Examples 6-17, infra. Plant growth promotion effects, from *Bacillus* sp. F727 and its metabolites, have also been observed on a number of plants. See Examples 18 and 19, infra.

Thus *Bacillus* sp. F727, and/or its metabolites, can be used as natural products for the control of fungal and bacterial diseases in agriculture; and for promotion of plant growth.

Methods of Production

As noted above, compounds or metabolites may be obtained, are obtainable or can be derived from an organism having one or more identifying characteristics of a *Bacillus* F727 strain. The methods comprise cultivating these organisms and obtaining the compounds and/or compositions of the present invention by isolating these compounds from the culture of these organisms.

In particular, the organisms are cultivated in nutrient medium using methods known in the art. The organisms can be cultivated by shake flask cultivation, small scale or large scale fermentation (including but not limited to continuous, batch, fed-batch, or solid state fermentations) in laboratory or industrial fermentors performed in suitable medium and under conditions allowing cell growth. The cultivation can take place in suitable nutrient medium comprising carbon and nitrogen sources and inorganic salts, using procedures known in the art. Suitable media are available from commercial sources or can be prepared according to published compositions.

After cultivation, a supernatant, filtrate and/or extract of or derived from said *Bacillus* strain (e.g., *Bacillus* sp. F727) can be used in formulating a pesticidal composition.

Alternatively, after cultivation, the compounds and/or metabolites can be extracted from the culture broth.

The extract can be fractionated by chromatography. Chromatographic fractions can be assayed for toxic activity against, for example, fungi (e.g., *Botrytis, Sclerotinia, Rhizoctonia* & *Bipolaris*) using methods known in the art. Fractionation can be repeated one or more times using the same or different chromatographic methods.

In one embodiment, the compound produced is a compound that (i) has pesticidal activity; (ii) has a molecular weight of about 1020-1120 as determined by Liquid Chromatography/Mass Spectroscopy (LC/MS); (iii) has a High Pressure Liquid Chromatography (HPLC) retention time of about 6-15 minutes on a reversed phase C-18 HPLC column using a water:acetonitrile ($CH_3CN$) gradient solvent system (0-20 min; 90-0% aqueous $CH_3CN$, 20-24 min; 100% $CH_3CN$, 24-27 min; 0-90% aqueous $CH_3CN$, 27-30 min; 90% aqueous $CH_3CN$) at 0.5 mL/min flow rate and UV detection at 210 nm; and (iv) is optionally obtainable from a *Bacillus* species. The compound in one embodiment is a peptide.

In a specific embodiment, the compound "A" (i) is obtainable from a *Bacillus* species; (ii) is toxic to a pest; (iii) has a molecular weight of about 1020-1060 and more particularly, 1044 as determined by Liquid Chromatography/Mass Spectroscopy (LC/MS); (iv) has $^1$H NMR values of δ 7.15, 6.72, 4.81, 4.70, 4.65, 4.40, 4.35, 4.25, 4.15, 3.85, 3.65, 3.50, 3.22, 2.85, 2.80, 2.65, 2.45, 2.35, 2.30, 2.20, 1.95, 1.55, 1.31, 1.20, 0.85; and (v) has a High Pressure Liquid Chromatography (HPLC) retention time of about 6-12 minutes, more specifically about 8 minutes and even more specifically about 8.31 min on a reversed phase C-18 HPLC (Phenomenex, Luna 5μ C18(2) 100 A, 100×4.60 mm) column using a water:acetonitrile ($CH_3CN$) with a gradient solvent system (0-20 min; 90-0% aqueous $CH_3CN$, 20-24 min; 100% $CH_3CN$, 24-27 min; 0-90% aqueous $CH_3CN$, 27-30 min; 90% aqueous $CH_3CN$) at 0.5 mL/min flow rate and UV detection at 210 nm. In addition, Compound "A" reveals signals for 47 carbons, 72 hydrogens, 12 nitrogens, and 15 oxygens as determined by $^1$H NMR, $^{13}$C NMR & MS analyses. The $^1$H NMR spectrum displays characteristics of a typical peptide. Detailed analysis of Compound "A" by $^1$H NMR, $^{13}$C NMR, MS/MS and amino acid analysis revealed the presence of glutamine (1 unit), proline (1 unit), serine (1 unit), tyrosine (1 unit) and asparagine (3 units).

In another particular embodiment, the substance may be a compound "B" that (i) has pesticidal activity; (ii) has a molecular weight of about 1030-1080 and more particularly, 1058 as determined by Liquid Chromatography/Mass Spectroscopy (LC/MS); and (iii) has a High Pressure Liquid Chromatography (HPLC) retention time of about 6-14 minutes, more specifically about 8 minutes and even more specifically about 8.67 min on a reversed phase C-18 HPLC column using a water:acetonitrile ($CH_3CN$) gradient solvent system (0-20 min; 90-0% aqueous $CH_3CN$, 20-24 min; 100% $CH_3CN$, 24-27 min; 0-90% aqueous $CH_3CN$, 27-30 min; 90% aqueous $CH_3CN$) at 0.5 mL/min flow rate and UV detection at 210 nm. Data from the $^1$H and $^{13}$C NMR spectra, along with MS data, reveal signals for 48 carbons, 74 hydrogens, 12 nitrogens, and 15 oxygens. The $^1$H NMR spectrum displays characteristics of a typical peptide. Detailed analysis of Compound "B" by $^1$H NMR, $^{13}$C NMR, MS/MS and amino acid analysis revealed the presence of glutamine (1 unit), proline (1 unit), serine (1 unit), tyrosine (1 unit) and asparagine (3 units).

In yet another particular embodiment, the substance may be a compound "C" that (i) has pesticidal activity; (ii) has a molecular weight of about 1050-1120 and more particularly, 1072 as determined by Liquid Chromatography/Mass Spectroscopy (LC/MS); and (iii) has a High Pressure Liquid Chromatography (HPLC) retention time of about 6-14 minutes, more specifically about 9 minutes and even more specifically about 9.19 min on a reversed phase C-18 HPLC column using a water:acetonitrile ($CH_3CN$) gradient solvent system (0-20 min; 90-0% aqueous $CH_3CN$, 20-24 min; 100% $CH_3CN$, 24-27 min; 0-90% aqueous $CH_3CN$, 27-30 min; 90% aqueous $CH_3CN$) at 0.5 mL/min flow rate and UV detection at 210 nm. Data from the $^1$H and $^{13}$C NMR spectra, along with MS data, reveal signals for 49 carbons, 76 hydrogens, 12 nitrogens, and 15 oxygens. The $^1$H NMR spectrum displays characteristics of a typical peptide. Detailed analysis of Compound "C" by $^1$H NMR, $^{13}$C NMR, MS/MS and amino acid analysis revealed the presence of glutamine (1 unit), proline (1 unit), serine (1 unit), tyrosine (1 unit) and asparagine (3 units).

Compositions

Compositions can comprise whole broth cultures, liquid cultures, or suspensions of or derived from a *Bacillus* strain, specifically a *Bacillus* strain having at least one of the identifying characteristics of *Bacillus* sp. isolate F727, as well as supernatants, filtrates or extracts obtained from said *Bacillus* sp. Compositions can also comprise one or more metabolites or isolated compounds derived from *Bacillus* sp. isolate F727, which in particular have bactericidal, fungicidal and/or plant growth-promoting activity.

The compositions set forth above can be formulated in any manner. Exemplary formulations include but are not limited to emulsifiable concentrates (EC), wettable powders (WP), soluble liquids (SL), aerosols, ultra-low volume concentrate solutions (ULV), soluble powders (SP), microencapsulates, water-dispersed granules, flowables (FL), microemulsions (ME), nano-emulsions (NE), etc. In any formulation described herein, percent of the active ingredient is within a range of 0.01% to 99.99%.

The compositions can be in the form of a liquid, gel or solid. A solid composition can be prepared by suspending a solid carrier in a solution of active ingredient(s) and drying the suspension under mild conditions, such as evaporation at room temperature or vacuum evaporation at 65° C. or lower.

A composition can comprise gel-encapsulated active ingredient(s). Such gel-encapsulated materials can be prepared by mixing a gel-forming agent (e.g., gelatin, cellulose, or lignin) with a culture or suspension of live or inactivated *Bacillus* sp. strain F727 cells, or with a cell-free filtrate or cell fraction of a *Bacillus* sp. strain F727 culture or suspension, or with a spray- or freeze-dried culture, cell, or cell fraction of *Bacillus* sp. strain F727; or with a solution of pesticidal compounds used in the method of the invention; and inducing gel formation of the agent.

The composition can additionally comprise a surfactant to be used for the purpose of emulsification, dispersion, wetting, spreading, integration, disintegration control, stabilization of active ingredients, and improvement of fluidity or rust inhibition. In a particular embodiment, the surfactant is a non-phytotoxic non-ionic surfactant which preferably belongs to EPA List 4B. In another particular embodiment, the nonionic surfactant is polyoxyethylene (20) monolaurate. The concentration of surfactant(s) can range between 0.1-35% of the total formulation, a preferred range is 5-25%. The choice of dispersing and emulsifying agents, such as non-ionic, anionic, amphoteric and cationic dispersing and emulsifying agents, and the amount employed, is determined by the nature of the composition and the ability of the agent to facilitate the dispersion of the compositions.

The compositions set forth above can be combined with another agent, microorganism and/or pesticide (e.g., nematicide, bactericide, fungicide, acaricide, insecticide). Microorganisms include but are not limited to *Bacillus* sp. (e.g., *Bacillus firmus, Bacillus thuringiensis, Bacillus pumilus, Bacillus licheniformis, Bacillus amyloliquefaciens, Bacillus subtilis*), *Paecilomyces* sp. (*P. lilacinus*), *Pasteuria* sp. (*P. penetrans*), *Chromobacterium* sp., *Pseudomonas* sp., *Brevabacillus* sp., *Lecanicillium* sp., *Ampelomyces* sp., *Pseudozyma* sp., *Streptomyces* sp (*S. bikiniensis, S. costaricanus, S. avermitilis*), *Burkholderia* sp., *Trichoderma* sp., *Gliocladium* sp., avermectin, *Myrothecium* sp., *Paecilomyces* spp., *Sphingobacterium* sp., *Arthrobotrys* sp., *Chlorosplrnium, Neobulgaria, Daldinia, Aspergillus, Chaetomium, Lysobacter* spp, *Lachnum papyraceum, Verticillium suchlasporium, Arthrobotrys oligospora, Verticillium chlamydosporium, Hirsutella rhossiliensis, Pochonia chlamydosporia, Pleurotus ostreatus, Omphalotus olearius, Lampteromyces japonicas, Brevudimonas* sp., *Muscodor* sp.

The agent can be a natural oil or oil-product having nematicidal, fungicidal, bactericidal and/or insecticidal activity (e.g., paraffinic oil, tea tree oil, lemongrass oil, clove oil, cinnamon oil, citrus oil, rosemary oil, pyrethrum, citrus oil (including but not limited to bitter orange, orange, and lemon oils); rosemary oil, allspice, bergamot, blue gum, chamomile, citronella, common jasmine, common juniper, common lavender, common myrrh, field mint, freesia, gray santolina, herb hyssop, holy basil, incense tree, jasmine, lavender, marigold, mint, peppermint, pot marigold, spearmint, ylang-ylang tree, saponins)

Furthermore, the pesticide can be a single site anti-fungal agent which can include but is not limited to benzimidazole, a demethylation inhibitor (DMI) (e.g., imidazole, piperazine, pyrimidine, triazole), morpholine, hydroxypyrimidine, anilinopyrimidine, phosphorothiolate, quinone outside inhibitor, quinoline, dicarboximide, carboximide, phenylamide, anilinopyrimidine, phenylpyrrole, aromatic hydrocarbon, cinnamic acid, hydroxyanilide, antibiotic, polyoxin, acylamine, phthalimide, benzenoid (xylylalanine); a demethylation inhibitor selected from the group consisting of imidazole, piperazine, pyrimidine and triazole (e.g., bitertanol, myclobutanil, penconazole, propiconazole, triadimefon, bromuconazole, cyproconazole, diniconazole, fenbuconazole, hexaconazole, tebuconazole, tetraconazole), myclobutanil, and a quinone outside inhibitor (e.g., strobilurin). The strobilurin may include but is not limited to azoxystrobin, kresoxim-methoyl or trifloxystrobin. In yet another particular embodiment, the anti-fungal agent is a quinone, e.g., quinoxyfen(5,7-dichloro-4-quinolyl 4-fluorophenyl ether). The anti-fungal agent can also be derived from a *Reynoutria* extract.

The fungicide can also be a multi-site non-inorganic, chemical fungicide selected from the group consisting of chloronitrile, quinoxaline, sulphamide, phosphonate, phosphite, dithiocarbamate, chloralkythios, phenylpyridin-amine and cyano-acetamide oxime.

As noted above, the composition can further comprise a nematicide. The nematicide can include but is not limited to chemicals such as organophosphates, carbamates, and fumigants, and microbial products such as avermectin, *Myrothecium* sp. Biome (*Bacillus firmus*), *Pasteuria* spp., *Paecilomyces*, and organic products such as saponins and plant oils.

The compositions can be applied using methods known in the art. Specifically, these compositions are applied to and around plants or plant parts. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including transgenic plants and plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. Plant parts also include harvested material, and vegetative and generative propagation material, for example cuttings, tubers, rhizomes, offshoots and seeds.

Treatment of plants and plant parts with the compositions set forth above can be carried out directly or by allowing the compositions to act on a plant's surroundings, habitat or storage space by, for example, immersion, spraying, evaporation, fogging, scattering, painting on, or injecting.

The compositions disclosed herein can also be applied to soil using methods known in the art. These include but are not limited to (a) drip irrigation or chemigation; (b) soil incorporation; (c) soil drenching; (d) seed treatment and dressing; and (e) bare root dip.

Seed Treatments

Seed treatments include application of a composition as disclosed herein, optionally in combination with other bioactive, antagonistic or symbiotic agents to the surface of a seed prior to sowing. Pesticidal toxins, proteins, and/or compounds disclosed herein can be applied to seeds as dry powders, slurried powders or sprayed on the seed before planting.

The compositions disclosed herein can be formulated for seed treatments in any of the following modes: dry powder, water slurriable powder, liquid solution, flowable concentrate or emulsion, emulsion, microcapsules, gel, or water dispersible granules.

In the case of a dry powder, the active ingredient is formulated similarly to a wettable powder, but with the addition of a sticking agent, such as mineral oil, instead of a wetting agent. For example, one kg of purified talc powder (sterilized for 12 h), 15 g calcium carbonate, and 10 g carboxymethyl cellulose are mixed under aseptic conditions following the method described by Nandakumar et al (2001). Active ingredient(s) is/are mixed in a 1:2.5 ratio (suspension to dry mix) and the product is shade dried to reduce moisture content to 20-35%.

In embodiments in which the compositions disclosed herein are applied to a seed, a composition can be applied as one or more coats prior to planting the seed using one or more seed coating agents including, but not limited to, ethylene glycol, polyethylene glycol, chitosan, carboxymethyl chitosan, peat moss, resins and waxes. The compositions can also be applied to seeds in combination with, for example, chemical fungicides or bactericides with a single site, multisite or unknown mode of action, using methods known in the art.

In additional embodiments, the disclosed compositions can be applied to seeds by seed imbibition or as a powdered inoculum.

The seeds may be conventional seeds or may be genetically modified seed such as Liberty Link (Bayer CropScience), Roundup Ready seeds (Monsanto), or other herbicide resistant seed, and/or seeds engineered to be insect resistant, or seeds that are with "pyrimaded" with herbicide and insect resistance genes.

Plant Growth Promotion

Plant-bacterial interactions in the rhizosphere are important determinants of soil fertility and plant health. Free living bacteria that are beneficial to plant growth are known as plant growth promoting rhizobacteria (PGPR). Generally plant growth promoters function in one of three ways: by synthesizing plant growth regulators, by facilitating the uptake of soil nutrients and/or by preventing plant disease. Therefore, the effects of PGPRs can be both direct and indirect. Indirect plant growth promotion can involve antagonistic effect against phytophatogens. This can be achieved, for example, by production of siderophores, synthesis of antibiotics, and the production of HCN and/or cell wall degrading enzymes. Direct plant growth promotion effects are achieved through the regulation of phytohormones (that help in plant and root development and protection against stresses), and solubilization of mineral phosphates and other nutrients.

The compositions disclosed herein, in particular, *Bacillus* sp. isolate F727 and/or a supernatant, filtrate, extract, compound, metabolite or cell fraction obtained from a culture of *Bacillus* sp. F727, can be used to modulate or more particularly promote growth of plants, e.g. crops such as fruit (e.g., strawberry), vegetable (e.g., tomato, squash, pepper, eggplant), legumes or grain crops (e.g., soy, wheat, rice, corn), tree, flower, ornamental plants, shrubs (e.g., cotton, roses), turf (e.g., annual rye grass, Bermuda grass, buffalo grass, colonial bentgrass, creeping bentgrass, dichondra, hard fescue, Kentucky bluegrass, kikuyugrass, perennial ryegrass, red fescue, rough bluegrass, seashore paspalum, St. Augustine grass, tall fescue, zoysiagrass, etc.), bulb plants (e.g., onion, garlic) or vine (e.g., grape vine). The compositions can also be used to modulate the germination of a seed(s) in a plant(s).

The compositions disclosed herein, or formulated product, can be used alone or in combination with one or more other components as described below, such as growth promoting agents and/or anti-phytopathogenic agents in a tank mix or in a program (sequential application called rotation) with predetermined order and application interval during the growing season. When used in a combination with the above-mentioned products, at a concentration lower than recommended on the product label, the combined efficacy of the two or more products (one of which is the said composition disclosed herein) is, in certain embodiments, greater than the sum of each individual component's effect. Hence, the effect is enhanced by synergism between these two (or more) products, and the risk for the development of pesticide resistance among the plant pathogenic strains is reduced.

The composition can be applied by root dip at transplanting, specifically by treating a fruit or vegetable with the composition by dipping roots of the fruit or vegetable in a suspension of said composition (about 0.25 to about 1.5% and more particularly about 0.5% to about 1.0% by volume) prior to transplanting the fruit or vegetable into the soil.

Alternatively, the composition can be applied by drip or other irrigation system. Specifically, the composition can be injected into a drip irrigation system. In a particular embodiment, the composition is applied at a concentration of $1\times10^8$ colony-forming units (CFU)/ml in a volume of approximately 11 to approximately 4 quarts per acre.

In yet another embodiment, the composition can be added as an in-furrow application. Specifically, the composition can be added as an in-furrow spray at planting using nozzles calibrated to deliver a total output of 2-6 gallons/acre. Nozzles are placed in the furrow opener on the planter so that the pesticide application and seed drop into the furrow are simultaneous.

Mixtures of the disclosed compositions with, for example, a solid or liquid adjuvant are prepared in known manner. For example, mixtures can be prepared by homogeneously mixing and/or grinding the active ingredients with extenders such as solvents, solid carriers and, where appropriate, surface-active compounds (surfactants). The compositions can also contain additional ingredients such as stabilizers, viscosity regulators, binders, adjuvants as well as fertilizers or other active ingredients in order to obtain special effects.

Combinations with Plant Growth Promoting Agents

The compositions disclosed herein can be used in combination with other growth promoting agents such as synthetic or organic fertilizers (e.g., di-ammonium phosphate, in either granular or liquid form), compost teas, seaweed extracts, plant growth hormones such as IAA (indole acetic acid) used in a rooting hormone treatment for transplants either alone or in combination with plant growth regulators such as IBA (indole butyric acid) and NAA (naphthalene acetic acid), and growth promoting microbes, such as, for example, PPFM (pink pigmented facultative methylotrophs), *Bacillus* spp., *Pseudomonads, Rhizobia*, and *Trichoderma*.

Anti-Phytopathogenic Agents

The compositions disclosed herein can also be used in combination with other anti-phytopathogenic agents, such as plant extracts, biopesticides, inorganic crop protectants (such as copper), surfactants (such as rhamnolipids; Gandhi et al., 2007) or natural oils such as paraffinic oil and tea tree oil possessing pesticidal properties or chemical fungicides or bactericides with either single site, multisite or unknown mode of action. As defined herein, an "anti-phytopathogenic agent" is an agent that modulates the growth of a plant pathogen, particularly a pathogen causing soil-borne disease on a plant, or alternatively prevents infection of a plant by a plant pathogen. A plant pathogen includes but is not limited to a fungus, bacteria, actinomycete or virus.

As noted above, the anti-phytopathogenic agent can be a single-site anti-fungal agent which can include but is not limited to benzimidazole, a demethylation inhibitor (DMI) (e.g., imidazole, piperazine, pyrimidine, triazole), morpholine, hydroxypyrimidine, anilinopyrimidine, phosphorothiolate, quinone outside inhibitor, quinoline, dicarboximide, carboximide, phenylamide, anilinopyrimidine, phenylpyrrole, aromatic hydrocarbon, cinnamic acid, hydroxyanilide, antibiotic, polyoxin, acylamine, phthalimide, benzenoid (xylylalanine) In a more particular embodiment, the antifungal agent is a demethylation inhibitor selected from the group consisting of imidazole, piperazine, pyrimidine and triazole (e.g., bitertanol, myclobutanil, penconazole, propiconazole, triadimefon, bromuconazole, cyproconazole, diniconazole, fenbuconazole, hexaconazole, tebuconazole, tetraconazole). In a most particular embodiment, the antifungal agent is myclobutanil. In yet another particular embodiment, the antifungal agent is a quinone outside inhibitor (e.g., strobilurin). The strobilurin may include but is not limited to azoxystrobin, kresoxim-methyl or trifloxystrobin. In yet another particular embodiment, the anti-fungal agent is a quinone, e.g., quinoxyfen(5,7-dichloro-4-quinolyl 4-fluorophenyl ether).

In yet a further embodiment, the fungicide is a multi-site non-inorganic, chemical fungicide selected from the group consisting of chloronitrile, quinoxaline, sulphamide, phosphonate, phosphite, dithiocarbamate, chloralkythios, phenylpyridine-amine, and cyano-acetamide oxime.

In yet a further embodiment, the anti-phytopathogenic agent can be streptomycin, tetracycline, oxytetracycline, copper, or kasugamycin.

EXAMPLES

Example 1

Isolation and Characterization of *Bacillus* sp. Isolate F727 by 16S rRNA, recA and phoR Sequences

*Bacillus* sp. strain F727 was isolated from a soil sample collected in Jonesville, Calif., using traditional plate dilution methods. The isolate was identified as a *Bacillus* sp. through PCR amplification and sequencing of the 16S rRNA, recA and phoR genes using universal bacterial primers. Cerritos et al. (2008) *Int. J. Sys. Evol. Microbiol.* 58:919-923; Guo et al. (2012) *Can. J. Microbiol.* 58: 1295-1305.

Growth from a 24 hour potato dextrose plate was scraped with a sterile loop and resuspended in DNA extraction buffer. DNA was extracted using the MoBio Ultra Clean Microbial DNA extraction kit. DNA extract was checked for quality/quantity by electrophoresis of a 5 uL aliquot on a 1% agarose gel.

rRNA Sequences

PCR reactions for the amplification of the 16S rRNA gene were set up by combining 2 μL of the clean DNA extract with 25 μL of GoTaq Green Mastermix, 1.5 μL forward primer (FD1 primer, 5'-AGAGTTTGATCCTGGCTCAG-3' (SEQ ID NO:4), and 1.5 μL reverse primer (RD1 primer, 5'-AAGGAGGTGATCCAGCC-3' (SEQ ID NO:5)). The reaction volume was adjusted to 50 μL with sterile nuclease-free water. The amplification reaction was conducted using a thermocycler machine under the following conditions: 10 minutes at 95° C. (initial denaturing), 30 cycles of 45 seconds at 94° C., 45 seconds at 55° C. and 2 minutes at 72° C., followed by 5 minutes at 72° C. (final extension) and a final hold temperature of 10° C.

The size, quality and quantity of the amplification product was evaluated by electrophoresis of a 5 uL aliquot on a 1% agarose gel, and comparison of the product band with a mass ladder.

Excess primers, nucleotides, enzyme and template were removed from the PCR product using the MoBio PCR clean up Kit. The cleaned PCR product was subjected to direct sequencing using the primers described above.

The forward and reverse sequences were aligned using the BioEdit software, and a 1459 bp consensus sequence was created.

F727 FD1 16S Sequence:
(SEQ ID NO: 1)
TATACATGCAAGTCGAGCGGACAGATGGGAGCTTGCTCCCTGATGTTAG

CGGCGGACGGGTGAGTAACACGTGGGTAACCTGCCTGTAAGACTGGGAT

AACTCCGGGAAACCGGGGCTAATACCGGATGCTTGTTTGAACCGCATGG

TTCAAACATAAAAGGTGGCTTCGGCTACCACTTACAGATGGACCCGCGG

CGCATTAGCTAGTTGGTGAGGTAACGGCTCACCAAGGCAACGATGCGTA

GCCGACCTGAGAGGGTGATCGGCCACACTGGGACTGAGACACGGCCCAG

ACTCCTACGGGAGGCAGCAGTAGGGAATCTTCCGCAATGGACGAAAGTC

TGACGGAGCAACGCCGCGTGAGTGATGAAGGTTTTCGGATCGTAAAGCT

CTGTTGTTAGGGAAGAACAAGTGCCGTTCGAATAGGGCGGCACCTTGAC

GGTACCTAACCAGAAAGCCACGGCTAACTACGTGCCAGCAGCCGCGGTA

ATACGTAGGTGGCAAGCGTTGTCCGGAATTATTGGGCGTAAAGGGCTCG

CAGGCGGTTTCTTAAGTCTGATGTGAAAGCCCCCGGCTCAACCGGGGAG

GGTCATTGGAAACTGGGGAACTTGAGTGCAGAAGAGGAGAGTGGAATTC

CACGTGTAGCGGTGAAATGCGTAGAGATGTGGAGGAACACCAGTGGCGA

AGGCGACTCTCTGGTCTGTAACTGACGCTGAGGAGCGAAAGCGTGGGGA

GCGAACAGGATTAGATACCCTGGTAGTCCACGCCGTAACGATGAGTGCT

AAGTGTTAGGGGGTTTCCGCCCCTTAGTGCTGCAGCTAACGCATTAAGC

ACTCCGCCTGGGGAGTACGGTCGCAAGACTGAAACTCAAAGGAATTGAC

GGGGGCCCGCACAAGCGGTGGAGCATGTGGTTTAATTCGAAGCAACGCN

AGAACCTTACCANGTCTTGACATCCTCTGACAATCCTAGAGATAGGACG

TCCCCTTCGGGGGCAGAGTGACNNNGGNGCATGGNNGTCGTCAGCTCGT

GTCGTGAGATGTTGGGTAAGTCCCGCACNAGCGCAACCCNTTGATCTTA

NTTGCCAGCATTCANTTGGNNNNNNNNNNNNNACTGCCNNNACNANCCG

NNNAAGGNNNNGGGNATNACGTNNANNNATNCNNGCCCNNNNTGACNNNN

NNCACNCCNNNNNNNNNNNANNGNNNNNNAANNANNGGGNCNNNNNGNNN

NNNNAAANNNCNNNCNCNNNNGNGNN

F727 RD1 16S Sequence::
(SEQ ID NO: 2)
TCATCTGTCCCACCTTCGGCGGCTGGCTCCATAAAGGTTACCTCACCGA
CTTCGGGTGTTACAAACTCTCGTGGTGTGACGGGCGGTGTGTACAAGGC
CCGGGAACGTATTCACCGCGGCATGCTGATCCGCGATTACTAGCGATTC
CAGCTTCACGCAGTCGAGTTGCAGACTGCGATCCGAACTGAGAACAGAT
TTGTGGGATTGGCTTAACCTCGCGGTTTCGCTGCCCTTTGTTCTGTCCA
TTGTAGCACGTGTGTAGCCCAGGTCATAAGGGGCATGATGATTTGACGT
CATCCCCACCTTCCTCCGGTTTGTCACCGGCAGTCACCTTAGAGTGCCC
AACTGAATGCTGGCAACTAAGATCAAGGGTTGCGCTCGTTGCGGGACTT
AACCCAACATCTCACGACACGAGCTGACGACAACCATGCACCACCTGTC
ACTCTGCCCCCGAAGGGGACGTCCTATCTCTAGGATTGTCAGAGGATGT
CAAGACCTGGTAAGGTTCTTCGCGTTGCTTCGAATTAAACCACATGCTC
CACCGCTTGTGCGGGCCCCCGTCAATTCCTTTGAGTTTCAGTCTTGCGA
CCGTACTCCCCAGGCGGAGTGCTTTAATGCGTTAGCTGCAGCACTAAGG
GGCGGAAACCCCCTAACACTTAGCACTCATCGTTTTACGGCGTGGACTA
CCAGGGTATCTAATCCTGTTCGCTCCCCACGCTTTCGCTCCCTCAGCG
TCAGTTACAGACCCAGAGAGTCGCCTTCGCCCACTGGTGTTCCTCCAC
ATCCTCTACGCATTTCACCCGGCTACAACGTGGAATTCCACTCTCCTCT
TCTGCACTCAAGTTTCCCCAGTTTCCAATGACCCCTCCCCGGTTGAGCC
CGGGGGCTTTCACATCAGACTTAAAGAAACCCGCCTGCGAGCCCTTTAC
GCCCAATAATTCCGGACACGCTTGGCCACCTACGTATTACCGCGCTTGC
TTGGCACGTTAGTAGCCGTGGCTTTTCTGGTTAGTTAACCGTCAGTGCC
GCCTATTCGGAACGGTACTTGTTCTTCCCTACACAGAGCTTTACGATCG
AAACTCATCACCTCCACGCGCGTGCTCGTCAGAACTTTCGTCATGCGAA
GATCCTACTGCTGCCTCCGTAGGGTTGGCGTTTCTCTCAGTCCAGTGGC
CATACGTCAGTAGCTACCCATCGTGCCTAGTGAGCGTTACCTCACCCAC
CTAGGC F727 Consensus 16S Sequence:
(SEQ ID NO: 3)
TATACATGCAAGTCGAGCGGACAGATGGGAGCTTGCTCCCTGATGTTAG
CGGCGGACGGGTGAGTAACACGTGGGTAACCTGCCTGTAAGACTGGGAT
AACTCCGGGAAACCGGGGCTAATACCGGATGCTTGTTTGAACCGCATGG
TTCAAACATAAAAGGTGGCTTCGGCTACCACTTACAGATGGACCCGCGG
CGCATTAGCTAGTTGGTGAGGTAACGGCTCACCAAGGCAACGATGCGTA
GCCGACCTGAGAGGGTGATCGGCCACACTGGGACTGAGACACGGCCCAG
ACTCCTACGGGAGGCAGCAGTAGGGAATCTTCCGCAATGGACGAAAGTC
TGACGGAGCAACGCCGCGTGAGTGATGAAGGTTTTCGGATCGTAAAGCT
CTGTTGTTAGGGAAGAACAAGTGCCGTTCGAATAGGGCGGCACCTTGAC
GGTACCTAACCAGAAAGCCACGGCTAACTACGTGCCAGCAGCCGCGGTA
ATACGTAGGTGGCCAAGCGTTGTCCGGAATTATTGGGCGTAAAGGGCTC
GCAGGCGGGTTTCTTTAAGTCTGATGTGAAAGCCCCCGGGCTCAACCGG
GGAGGGGTCATTGGAAACTGGGGAAACTTGAGTGCAGAAGAGGAGAGTG
GAATTCCACGTTGTAGCCGGGTGAAATGCGTAGAGGATGTGGAGGAACA
CCAGTGGGGCGAAGGCGACTCTCTGGGTCTGTAACTGACGCTGAGGGAG
CGAAAGCGTGGGGGAGCGAACAGGATTAGATACCCTGGTAGTCCACGCC
GTAAACGATGAGTGCTAAGTGTTAGGGGGTTTCCGCCCCTTAGTGCTG
CAGCTAACGCATTAAAGCACTCCGCCTGGGGAGTACGGTCGCAAGACTG
AAACTCAAAGGAATTGACGGGGGCCCGCACAAGCGGTGGAGCATGTGGT
TTAATTCGAAGCAACGCGAAGAACCTTACCAGGTCTTGACATCCTCTGA
CAATCCTAGAGATAGGACGTCCCCTTCGGGGGCAGAGTGACAGGTGGTG
CATGGTTGTCGTCAGCTCGTGTCGTGAGATGTTGGGTTAAGTCCCGCAA
CGAGCGCAACCCTTGATCTTAGTTGCCAGCATTCAGTTGGGCACTCTAA
GGTGACTGCCGGTGACAAACCGGAGGAAGGTGGGGATGACGTCAAATCA
TCATGCCCCTTATGACCTGGGCTACACACGTGCTACAATGGACAGAACA
AAGGGCAGCGAAACCGCGAGGTTAAGCCAATCCCACAAATCTGTTCTCA
GTTCGGATCGCAGTCTGCAACTCGACTGCGTGAAGCTGGAATCGCTAGT
AATCGCGGATCAGCATGCCGCGGTGAATACGTTCCCGGGCCTTGTACAC
ACCGCCCGTCACACCACGAGAGTTTGTAACACCCGAAGTCGGTGAGGTA
ACCTTTATGGAGCCAGCCGCCGAAGGTGGGACAGATGA The 16S rRNA gene consensus sequence of strain F727 was compared to those available sequences of representatives of the bacterial domain using BLAST. The closest species match was to *Bacillus* sp. (accession number GU250449.1), with 99% similarity. No single 16S sequence in the publicly available databases showed a 100% similarity to strain F727.

Additionally, the consensus sequence was analyzed using the EzTaxon-e server (eztaxon-e.ezbiocloud.net/; Kim et al., 2012) on the basis of 16S rRNA sequence data. The closest matches (shown in Table 1) included type strains for several species of the genus *Bacillus* that cannot be differentiated based solely on 16S rRNA sequences.

TABLE 1

| Rank | Name | Strain | Authors | Accession | Pairwise Similarity (%) | Diff/Total nt | Completeness (%) |
|---|---|---|---|---|---|---|---|
| 1 | *Bacillus subtilis* subsp. *inaquosorum* | BGSC 3A28(T) | Rooney et al. 2009 | EU138467 | 99.66 | 4/1168 | 79.3 |
| 2 | *Brevibacterium halotolerans* | DSM 8802(T) | Delaporte and Sasson 1967 | AM747812 | 99.65 | 5/1442 | 100 |
| 3 | *Bacillus mojavensis* | RO-H-1(T) | Roberts et al. 1994 | JH600280 | 99.58 | 6/1442 | 100 |

TABLE 1-continued

| Rank | Name | Strain | Authors | Accession | Pairwise Similarity (%) | Diff/Total nt | Completeness (%) |
|---|---|---|---|---|---|---|---|
| 4 | Bacillus vallismortis | DV1-F-3(T) | Roberts et al. 1996 | JH600273 | 99.51 | 7/1442 | 100 |
| 5 | Bacillus tequilensis | 10b(T) | Gatson et al. 2006 | HQ223107 | 99.51 | 7/1427 | 98.5 |
| 6 | Bacillus siamensis | KCTC 13613(T) | Sumpavapol et al. 2010 | AJVF01000043 | 99.45 | 8/1442 | 100 |
| 7 | Bacillus subtilis subsp. subtilis | NCIB 3610(T) | (Ehrenberg 1835) Cohn 1872 | ABQL01000001 | 99.45 | 8/1442 | 100 |
| 8 | Bacillus sp. subsp. plantarum | FZB42(T) | Borriss et al. 2011 | CP000560 | 99.38 | 9/1442 | 100 |
| 9 | Bacillus subtilis subsp. spizizenii | NRRL B-23049(T) | Nakamura et al. 1999 | CP002905 | 99.38 | 9/1442 | 100 |
| 10 | Bacillus atrophaeus | JCM 9070(T) | Nakamura 1989 | AB021181 | 99.38 | 9/1442 | 100 |
| 11 | Bacillus sp. subsp. amyloliquefaciens | DSM 7(T) | Borris (ex Fukumoto 1943) Priest et al. 1987 | FN597644 | 99.31 | 10/1442 | 100 |
| 12 | Bacillus methylotrophicus | CBMB205 (T) | Madhaiyan et al. 2010 (Weigmann 1898) | EU194897 | 99.09 | 13/1434 | 98.3 |
| 13 | Bacillus licheniformis | ATCC 14580(T) | Chester 1901 | AE017333 | 98.06 | 28/1441 | 100 |
| 14 | Bacillus sonorensis | NRRL B-23154(T) | Palmisano et al. 2001 | AF302118 | 97.7 | 32/1389 | 95.7 |
| 15 | Bacillus aerius | 24K(T) | Shivaji et al. 2006 | AJ831843 | 97.36 | 38/1442 | 100 |
| 16 | Bacillus aerophilus | 28K(T) | Shivaji et al. 2006 | AJ831844 | 97.15 | 41/1441 | 100 |
| 17 | Bacillus altitudinis | 41KF2b(T) | Shivaji et al. 2006 | AJ831842 | 97.15 | 41/1441 | 100 |
| 18 | Bacillus stratosphericus | 41KF2a(T) | Shivaji et al. 2006 | AJ831841 | 97.15 | 41/1441 | 100 |
| 19 | Bacillus safensis | FO-036b(T) | Satomi et al. 2006 | AF234854 | 97 | 43/1434 | 97.5 | recA Sequences

PCR reactions for the amplification of the recA gene were assembled by combining 2 μL of the clean DNA extract with 25 μL of GoTaq Green Mastermix, 1.5 μL forward primer (recAf, 5'-GATCGTCARGCAGSCYTWGAT-3', SEQ ID NO:6), and 1.5 μL reverse primer (recAr, 5'-TTWCCRAC-CATAACSCCRAC-3', SEQ ID NO:7). The reaction volume was adjusted to 50 μL using sterile nuclease-free water. The amplification reaction was conducted on a thermocycler machine under the following conditions: 5 minutes at 95° C. (initial denaturing), 30 cycles of 30 seconds at 95° C., 30 seconds at 45° C. and 1 minute at 72° C., followed by 5 minutes at 72° C. (final extension) and a final hold temperature of 4° C.

The size, quality and quantity of the PCR product was evaluated by electrophoresis of a 54 aliquot on a 1% agarose gel, and comparison of the product band with a mass ladder.

Excess primers, nucleotides, enzyme and template were removed from the PCR product using the MoBio PCR clean up Kit. The cleaned PCR product was subjected to direct sequencing using the primers described above.

The forward and reverse sequences were aligned using the BioEdit software, and a 505 bp consensus sequence was created.

F727 Forward recA Sequence:
(SEQ ID NO: 8)
AACATTCGGCAAGGTTCCATCATGAAACTCGGGGAAAAGACGGATACAA

GAATTTCAACAGTTCCGAGCGGTTCCCTTGCACTTGATACCGCTCTCGG

AATAGGCGGATACCCGCGCGGACGGATTATTGAAGTATACGGACCTGAA

AGCTCAGGTAAAACGACTGTAGCGCTTCATGCGATTGCTGAAGTTCAGG

AGAAAGGCGGACAAGCCGCATTTATTGATGCTGAGCATGCCCTTGACCC

TGTTTACGCGCAAAAGCTCGGTGTAAATATTGAGGAGCTGCTGCTTTCT

CAGCCTGATACGGGAGAGCAGGCGCTTGAGATTGCCGAAGCGCTGGTAC

GAAGCGGAGCCGTCGATATCGTAGTTGTCGACTCTGTTGCGGCGCTTGT

CCCGAAAGCTGAAATCGAAGGAGACATGGGGGATTCCCACGTCGGTTTG

CAGGCCCGTTTGATGTCTCAAGCGCTCCGTAAGCTTTCCGGTGCCATCA

ATAAATCTAAAACAATCGCAATCTTTATTAACCAAATTCGTGAAAAAGT

CGGCGTTAGGGTCGGAAAAAA

F727 Reverse recA Sequence:
(SEQ ID NO: 9)
GTATAAGATTGCGATTGTTTTAGATTTATTGATGGCACCGGAAAGCTTA

CGGAGCGCTTGAGACATCAAACGGGCCTGCAAACCGACGTGGGAATCCC

CCATGTCTCCTTCGATTTCAGCTTTCGGGACAAGCGCCGCAACAGAGTC

-continued

```
GACAACTACGATATCGACGGCTCCGCTTCGTACCAGCGCTTCGGCAATC

TCAAGCGCCTGCTCTCCCGTATCAGGCTGAGAAAGCAGCAGCTCCTCAA

TATTTACACCGAGCTTTTGCGCGTAAACAGGGTCAAGGGCATGCTCAGC

ATCAATAAATGCGGCTTGTCCGCCTTTCTCCTGAACTTCAGCAATCGCA

TGAAGCGCTACAGTCGTTTTACCTGAGCTTTCAGGTCCGTATACTTCAA

TAATCCGTCCGCGCGGGTATCCGCCTATTCCGAGAGCGGTATCAAGTGC

AAGGGAACCGCTCGGAACTGTTGAAATTCTTGTATCCGTCTTTTCCCCG

AGTTTCATGATGGAACCTTTGCCGAATTGTTTTTCTATTTGCTTAAGAG

CCATATCWAAGRCTGWAWTRAMRATCAA
```

F727 Consensus recA Sequence:

(SEQ ID NO: 10)

```
AAGGTTCCATCATGAAACTCGGGGAAAAGACGGATACAAGAATTTCAAC

AGTTCCGAGCGGTTCCCTTGCACTTGATACCGCTCTCGGAATAGGCGGA

TACCCGCGCGGACGGATTATTGAAGTATACGGACCTGAAAGCTCAGGTA

AAACGACTGTAGCGCTTCATGCGATTGCTGAAGTTCAGGAGAAAGGCGG

ACAAGCCGCATTTATTGATGCTGAGCATGCCCTTGACCCTGTTTACGCG

CAAAAGCTCGGTGTAAATATTGAGGAGCTGCTGCTTTCTCAGCCTGATA

CGGGAGAGCAGGCGCTTGAGATTGCCGAAGCGCTGGTACGAAGCGGAGC

CGTCGATATCGTAGTTGTCGACTCTGTTGCGGCGCTTGTCCCGAAAGCT

GAAATCGAAGGAGACATGGGGGATTCCCACGTCGGTTTGCAGGCCCGTT

TGATGTCTCAAGCGCTCCGTAAGCTTTCCGGTGCCATCAATAAATCTAA

AACAATCGCAATCTT
```

The recA gene consensus sequence of strain F727 (SEQ ID NO:10) was compared to representative bacterial sequences using BLAST. The closest species match was to the complete genome of *Bacillus amyloliquefaciens* (accession number CP002927.1), with 92% similarity.

phoR Sequences

PCR reactions for the amplification of the phoR gene were assembled by combining 2 µL of the clean DNA extract with 25 µL of GoTaq Green Mastermix, 1.5 µL forward primer (phoR-f: 5'-TTYARYTCATGRGAVACATT-3', SEQ ID NO:11), and 1.5 µL reverse primer (phoR-r: 5'-GGN-TAYAAANARGAGGAGCC-3', SEQ ID NO:12). The reaction volume was adjusted to 50 µL using sterile nuclease-free water. The amplification reaction was conducted on a thermocycler machine under the following conditions: 5 minutes at 95° C. (initial denaturing), 35 cycles of 45 seconds at 95° C., 45 seconds at 48° C. and 1 minute at 72° C., followed by 10 minutes at 72° C. (final extension) and a final hold temperature of 4° C.

The size, quality and quantity of the PCR product was evaluated by electrophoresis of a 5 µL aliquot on a 1% agarose gel, and comparison of the product band with a mass ladder.

Excess primers, nucleotides, enzyme and template were removed from the PCR product using the MoBio PCR clean up Kit. The cleaned PCR product was subjected to direct sequencing using the primers described above.

A 998 nucleotide phoR sequence was obtained using the reverse primer described above.

F727 Reverse pHoR sequence:

(SEQ ID NO: 13)

```
TCGTTGTCTGTATCATATTGGTTTTCAGTGTTCTCGGCCTTTTCTTGCA

GCAGCTCATTTCTTCATCCGCCAAGGAAAGAACGGAGGGACAGCTTGAA

AAGGAAGCCGCATACATAGCCGGACTCCTTGACGCCGGCCAAGTAAACA

ATAAAAGAAACGAAACGGTCATTAAAGATGCCAGCCGTACATTAGATAT

CGACGTGTCCGTATTAAATGAAAAAGGCCGCGGTTTATATCACTCAGGC

AGACGCGCTGATGACTCGGCTATAAAGGAATTCGTCTCCCGTAATAAAA

ATGCGGCGGCGATTCAGAACGGAGAGAAAGTATGGCATGGAACGGCCCT

TAAAAACGCCGCCGGCCAAACGGCGGGATATGTGCTCGTTTCCTCGCGG

ATCGATAAAGGTTCGAATATAACAGGGGAAATGTGGGGCATGCTGGCTG

CAAGCCTTTGTACTGCTTTTATTATTATCGTTTTCTTCTATACGAATAT

GACCTCCCGTTACAAAAGGTCAATCGACTCCGCGACAAAAGTGGCCACT

GAGCTGTCTAAGGGGAACTATGACGCCCGCTCCTACGGCGGGTACGCAA

GACGCTCAGACCGTCTCGGGCGCGCTATGAACAGCCTCGCTGTGGATTT

GATGGAAATGACGAGAACGCAGGATATGCAGCGCGACCGCCTGCTGACC

GTCATCGAAAATATCGGATCAGGTTTGATTTTAATAGACGGGAGAGGCT

TTATTAATCTCGTGAACAGGTCGTATACGAAGCAGTTCCATACAAATCC

TGAACGTCTGCTTCGGCGTCTCTACCATGACGCATTTGAGCATGAGGAA

ATCATTCGGCTGGTCGAAGACATCTTTATGCAGAAACGAAGAAACGCC

AGCTGCTCACGCTTCCCATCAAAATCGAACGGCGCTATTTTGAGGTTGA

CGGCGTCCCGATTATGGGCCCTGACGATGAATGGAAAAGGCATTGTTCT

CGTGTTTCATGATATGAC
```

The phoR reverse sequence was compared to representative bacterial sequences using BLAST. The closest species match was to the complete genome of several *Bacillus amyloliquefaciens* strains with only 83% similarity.

Example 2

Fatty Acid Composition of Isolate F727

A fatty acid profile of isolate F727 was performed at MIDI Labs, Inc (Newark, Del.), according to commercial standards. Results are shown in Table 2. Comparison of its fatty acid profile to the RTSBA6 6.10 fatty acid database showed that isolate F727 had a similarity index of 0.885 with *Bacillus subtilis*.

TABLE 2

| Fatty Acid | % |
| --- | --- |
| 13:0 iso | 0.44 |
| 13:0 anteiso | 0.32 |
| 14:0 iso | 1.09 |
| 14:0 | 0.45 |
| 15:0 iso | 26.19 |
| 15:0 anteiso | 37.58 |
| 16:1 w7c OH | 0.56 |
| 16:0 iso | 2.57 |
| 16:1w11c | 2.53 |
| 16:0 | 2.99 |
| 17:1w10c | 2.92 |
| Sum 4 | 0.82 |
| 17:0 iso | 12.59 |

TABLE 2-continued

| Fatty Acid | % |
|---|---|
| 17:0 anteiso | 8.71 |
| 18:0 | 0.23 |

Example 3

Characterization of Isolate F727 by MALDI-TOF Protein Profile

A MALDI-TOF mass spectroscopic protein fingerprint of isolate F727 was performed at MIDI Labs, Inc. (Newark, Del.). Isolate F727 displayed a MALDI-TOF protein profile unlike that of any other microorganism present in the database of mass spectra. Some similarities with protein profiles of *Bacillus vallismortis, Bacillus mojaviensis* and *Bacillus subtilis* were observed; however, none of the similarity scores were high enough to be indicative of even a generic match.

Example 4

Biochemical Characterization of *Bacillus* sp. Isolate F727

Gram Stain

Gram staining is a method of differentiating bacteria based on the physical properties of the cell wall, primarily the composition of peptidoglycan. Gram-positive bacterial isolates have a thick peptidoglycan layer resulting in a purple/blue staining; whereas gram-negative bacterial isolates have a thinner peptidoglycan layer in the cell wall, resulting in a red/pink staining Microscopic inspection of isolate F727 after Gram staining revealed purple cells, indicating that *Bacillus* sp. isolate F727 is a Gram-positive bacterium.

Urease Activity

The urease test is used to detect the activity of the enzyme urease, which catalyzes the conversion of urea to ammonia and bicarbonate. The urea broth contains urea and the pH indicator phenol red. The indicator turns yellow in an acidic environment and pink in an alkaline environment. If urease enzymatic activity is present, the urea in the broth is degraded to produce ammonia, and the medium turns pink, indicating a positive test.

After inoculation with isolate F727, urea broth changed color from red to yellow, indicating a negative test for urease activity. Thus, *Bacillus* sp. isolate F727 created an acidic environment, indicative of the absence of urease activity.

Catalase Activity

The catalase test is used to detect the activity of the enzyme, catalase. Catalase breaks down hydrogen peroxide into oxygen and water. Organisms that possess catalase activity produce gas bubbles when treated with hydrogen peroxide. Bubbles formed within seconds of applying the reagent to a culture of *Bacillus* sp. isolate F727, indicating that this organism possesses catalase activity.

Oxidase Activity

The oxidase test is used to detect the presence of cytochrome c oxidase activity. Bacteria that contain cytochrome c as part of their respiratory chain are oxidase-positive and turn the reagent purple. Conversely, bacteria that are oxidase negative do not oxidize the reagent, leaving it colorless. *Bacillus* sp. isolate F727 turned the reagent purple, demonstrating that it possessed oxidase activity.

TSI Agar

Triple sugar iron (TSI) agar is used to determine the ability of a microorganism to ferment glucose, lactose and/or sucrose, as well as the ability of enteric bacteria to produce hydrogen sulfide. The medium contains the pH indicator phenol red as well as ferrous sulfate, which reacts with hydrogen sulfide to produce a black precipitate. When isolate F727 was tested, the slant remained red while the butt changed from red to yellow, and no black color was observed. These results indicate that isolate F727 does not produce hydrogen sulfide and ferments only glucose, not lactose or sucrose.

Antibiotic Susceptibility

Antibiotic susceptibility of *Bacillus* sp. isolate F727 was tested using antibiotic discs on Muller-Hinton medium. A loopful of F727 was resuspended in 1 mL of sterile deionized water, and 100 µL of this suspension was streaked onto a Mueller-Hinton agar plate. After absorption of the streak into the agar, pre-loaded antibiotic discs were placed on the plate, and the plate was incubated at 25° C. for 48 hours. Results are presented in Table 3.

TABLE 3

Susceptibility of *Bacillus* sp. F727 to various antibiotics

| | Concentration (ug) | Susceptibility* |
|---|---|---|
| Tetracycline | 30 | +++ |
| Kanamycin | 30 | +++ |
| Erythromycin | 15 | +++ |
| Streptomycin | 10 | ++ |
| Penicillin | 10 | +++ |
| Ampicillin | 10 | +++ |
| Oxytetracycline | 30 | +++ |
| Chloramphenicol | 30 | +++ |
| Ciprofloxacin | 5 | +++ |
| Gentamicin | 10 | +++ |
| Piperacillin | 100 | +++ |
| Cefuroxime | 30 | +++ |
| Imipenem | 10 | +++ |
| Sulphamethoxazole-Trimethoprim | 23.75/25 | +++ |

*+++ indicates highly susceptible (no growth); ++ indicates moderately susceptible (reduced growth); − indicates no susceptibility API ZYM Strip The API ZYM strip (BioMerrieux) provides a method for testing various enzymatic activities of a microbe. The assay was carried out according to the manufacturer's instructions, and a summary of the results is shown in Table 4.

TABLE 4

| | Enzyme assayed | | | Interpretation | | |
|---|---|---|---|---|---|---|
| No. | for | Substrate | pH | Positive | Negative | Results |
| 1 | Control | | 8.5 | Colorless or color of the sample if it has intense coloration | | − |
| 2 | Alkaline phosphatase | 2-naphthyl phosphate | 6.5 | Violet | Colorless or very | ++ |
| 3 | Esterase (C 4) | 2-naphythyl butyrate | 7.5 | Violet | pale yellow | ++ |

TABLE 4-continued

| No. | Enzyme assayed for | Substrate | pH | Positive | Negative | Results |
|---|---|---|---|---|---|---|
| 4 | Esterase Lipase (C 8) | 2-naphthyl caprylate | 7.5 | Violet | | + |
| 5 | Lipase (C 14) | 2-naphthyl myristate | 7.5 | Violet | | − |
| 6 | Leucine arylamidase | L-leucyl-2-naphthylamide | 7.5 | Orange | | + |
| 7 | Valine arylamidase | L-valyl-2-naphthylamide | 7.5 | Orange | | + |
| 8 | Cysteine arylamidase | L-cystyl-2-naphthylamide | 7.5 | Orange | | − |
| 9 | Trypsin | N-benzoyl-DL-arginine-2-naphthylamide | 8.5 | Orange | | − |
| 10 | α-chymotrypsin | N-glutaryl-phenylalanine-2-naphthylamide | 7.5 | Orange | | − |
| 11 | Acid phosphatase | 2-naphthyl phosphate | 5.4 | Violet | | +++ |
| 12 | Naphthol-AS-BI-phosphohydrolase | Naphthol-AS-BI-phosphate | 5.4 | Blue | | +++ |
| 13 | α-galactosidase | 6-Br-2-naphthyl-αD-galactopyranoside | 5.4 | Violet | | − |
| 14 | β-galactosidase | 2-naphthyl-βD-galactopyranoside | 5.4 | Violet | | − |
| 15 | β-glucuronidase | Naphthol-AS-BI-βD-glucuronide | 5.4 | Blue | | − |
| 16 | α-glucosidase | 2-naphthyl-αD-glucopyranoside | 5.4 | Violet | | − |
| 17 | β-glucosidase | 6-Br-2-naphthyl-βD-glucopyranoside | 5.4 | Violet | | − |
| 18 | N-acetyl-β-glucosaminidase | 1-naphthyl-N-acetyl-βD-glucosaminide | 5.4 | Brown | | − |
| 19 | α-mannosidase | 6-Br-2-naphthyl-αD-mannopyranoside | 5.4 | Violet | | − |
| 20 | α-fucosidase | 2-naphthyl-αL-fucopyranoside | 5.4 | Violet | | − |

API 20 NE Strip

The API® 20 NE strip consists of 20 microtubes that contain dehydrated substrates. The conventional tests were inoculated with a *Bacillus* sp. isolate F727 suspension which reconstitutes the medium. Metabolism produced color changes in the microtubes. The assimilation tests were inoculated with a minimal medium and *Bacillus* sp. isolate F727 grows if the bacterium is capable of utilizing the substrate. The reactions were analyzed according to the manufacturer's reading table, and the results are summarized in Table 5.

TABLE 5

| Test | Active Ingredient | Reaction/Enzymes | Results Negative | Positive | Summary |
|---|---|---|---|---|---|
| NO₃ | Potassium Nitrate | Reduction of nitrates to nitrites | NIT 1 + NIT 2, read after 5 min Colorless Pink-Red | | + |
| | | Reduction of nitrates to nitrogen | ZN, read after 5 min Pink Colorless | | − |
| TRP | L-tryptophan | Indole production (tryptophan) | JAMES, read Immediately Colorless Pink | | − |
| GLU | D-glucose | Fermentation (glucose) | Pale-green/yellow Blue to green | Yellow | − |
| ADH | L-arginine | Arginine Dihydrolase | yellow | Orange/pink/red | − |
| URE | Urea | Urease | yellow | Orange/pink/red | − |
| ESC | Esculin ferric citrate | Hydrolysis (β-glucosidase)(esculin) | yellow | Grey/brown/black | + |
| GEL | Gelatin (bovine origin) | Hydrolysis (protease)(gelatin) | No pigment diffusion | Diffusion of black pigment | + |
| PNG | 4-nitrophenyl-βD-galactopyranoside | B-galactosidase (Para-nitrophenyl-βD-galactopyranosidase) | colorless | Yellow | − |
| |GLU| | D-glucose | Assimilation of glucose | Transparent | Opaque | + |
| |ARA| | L-arabinose | Assimilation of arabinose | Transparent | Opaque | − |
| |MNE| | D-mannose | Assimilation of mannose | Transparent | Opaque | − |
| |MAN| | D-mannitol | Assimilation of mannitol | Transparent | Opaque | + |
| |NAG| | N-acetyl-glucosamine | Assimilation of n-acetyl-glucosamine | Transparent | Opaque | + |
| |MAL| | D-maltose | Assimilation of maltose | Transparent | Opaque | + |

TABLE 5-continued

| | Active | | Results | | |
|---|---|---|---|---|---|
| Test | Ingredient | Reaction/Enzymes | Negative | Positive | Summary |
| |GNT| | Potassium gluconate | Assimilation of potassium gluconate | Transparent | Opaque | − |
| |CAP| | Capric acid | Assimilation of capric acid | Transparent | Opaque | − |
| |ADI| | Adipic acid | Assimilation of adipic acid | Transparent | Opaque | − |
| |MLT| | Malic acid | Assimilation of malate | Transparent | Opaque | + |
| |CIT| | Trisodium citrate | Assimilation of trisodium citrate | Transparent | Opaque | ± |
| |PAC| | Phenylacetic acid | Assimilation of phenylacetic acid | Transparent | Opaque | − |

Positive: +
Negative: −
Weak: ±

Example 5

Isolation and Characterization of Compounds A, B & C

Purification Procedure

The following procedure (outlined in FIG. 1) was used for the purification of compounds extracted from a cell culture of *Bacillus* sp. isolate F727.

The culture broth from a 1-L fermentation of *Bacillus* sp. isolate F727 in growth medium was extracted with Amberlite XAD-7 resin (Asolkar et al., 2006) by shaking the cell suspension with resin at 155 rpm for two hours at room temperature. The resin and cell mass were collected by filtration through cheesecloth and washed with deionized water to remove salts. The resin, cell mass, and cheesecloth were then soaked for 2 hours in acetone, after which the acetone was filtered and dried under vacuum, using a rotary evaporator, to provide a crude extract.

The crude extract was subjected to reversed-phase C18 vacuum liquid chromatography (VLC, $H_2O/CH_3OH$; gradient 80:20 to 0:100%) to yield 6 fractions. These fractions were concentrated to dryness using a rotary evaporator, and the resulting dry residues were screened for biological activity using an agar-disc assay. See Example 16 below. This assay identified C-18 VLC Fraction 3 as possessing fungicidal activity.

Active fraction 3 was subjected to reversed phase HPLC (Spectra System P4000, Thermo Scientific) to provide pure compounds, which were then screened in above mentioned bioassays to locate/identify the active compounds.

The active fraction 3 was purified further on a HPLC C-18 column (Phenomenex, Luna 10u C18(2) 100 A, 250×30) using a water:acetonitrile (containing 0.01% TFA) gradient solvent system (0-10 min; 70% aqueous $CH_3CN$, 10-20 min; 70-45% aqueous $CH_3CN$, 20-40 min; 45-30% aqueous $CH_3CN$, 40-60 min; 30-0% $CH_3CN$, 60-65 min; 100% $CH_3CN$, 65-70 min; 0-30% aqueous $CH_3CN$) at 8 mL/min flow rate with UV detection at 210 nm. Three purified compounds were obtained:

Compound A (F727F3H11), having a retention time of 35.95 min,

Compound B (F727F3H14), having a retention time of 37.26 min, and

Compound C (F727F3H17), having a retention time of 38.11 min.

Mass Spectroscopy

Mass spectroscopic analysis of compounds A, B and C was performed on a Thermo Finnigan LCQ Deca XP Plus electrospray (ESI) instrument using both positive and negative ionization modes in a full scan mode (m/z 100-1500 Da) on a LCQ DECA XPP$^{plus}$ Mass Spectrometer (Thermo Electron Corp., San Jose, Calif.). A Thermo high performance liquid chromatography (HPLC) instrument equipped with Finnigan Surveyor PDA plus detector, autosampler plus, MS pump and a 4.6 mm×100 mm Luna C18 5 μm column (Phenomenex) was used. The solvent system consisted of water (solvent A) and acetonitrile (solvent B). The mobile phase begins at 10% solvent B and is linearly increased to 100% solvent B over 20 min and then maintained at 100% Solvent B for 4 min, and finally returned to 10% solvent B over 3 min and maintained at 10% B for 3 min. The flow rate was 0.5 mL/min. The injection volume was 10 μL and the samples were kept at room temperature in an auto sampler.

The compounds were analyzed by LC-MS utilizing the LC and reversed phase chromatography. Mass spectroscopic analysis of the present compounds was performed under the following conditions: the flow rate of nitrogen gas was fixed at 30 and 15 arb for the sheath and aux/sweep gas flow rate, respectively. Electrospray ionization was performed with a spray voltage set at 5000 V and a capillary voltage at 35.0 V. The capillary temperature was set at 400° C. The data was analyzed on Xcalibur software.

Figure 2:
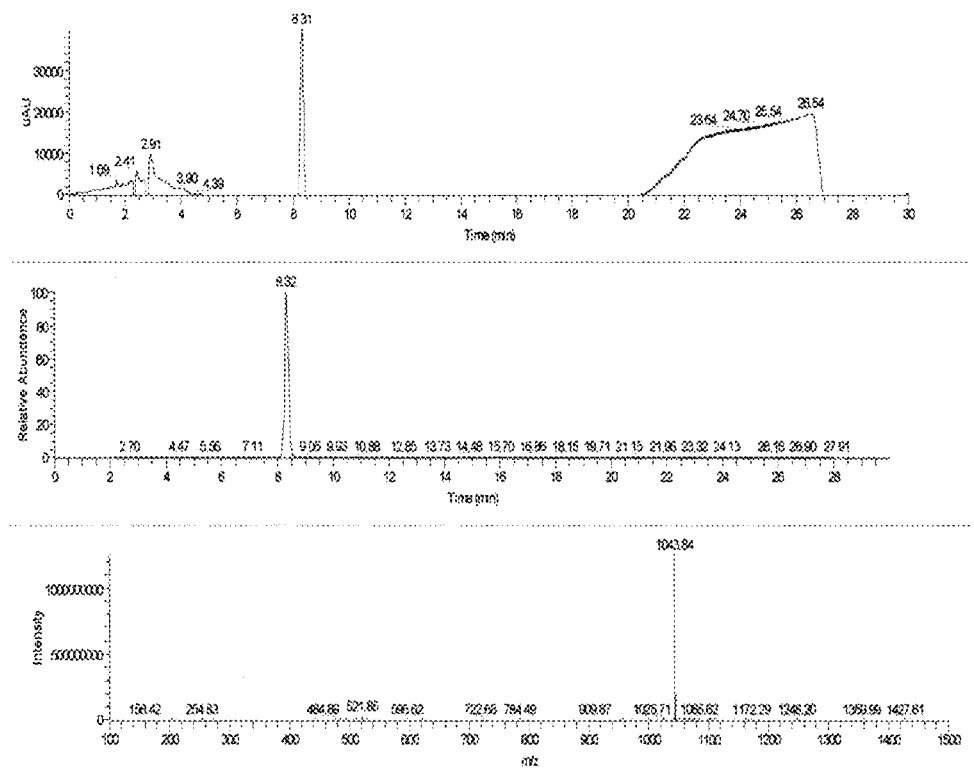
FIG. 2 depicts the ESI-LCMS chromatogram for compound "A".
Figure 3:
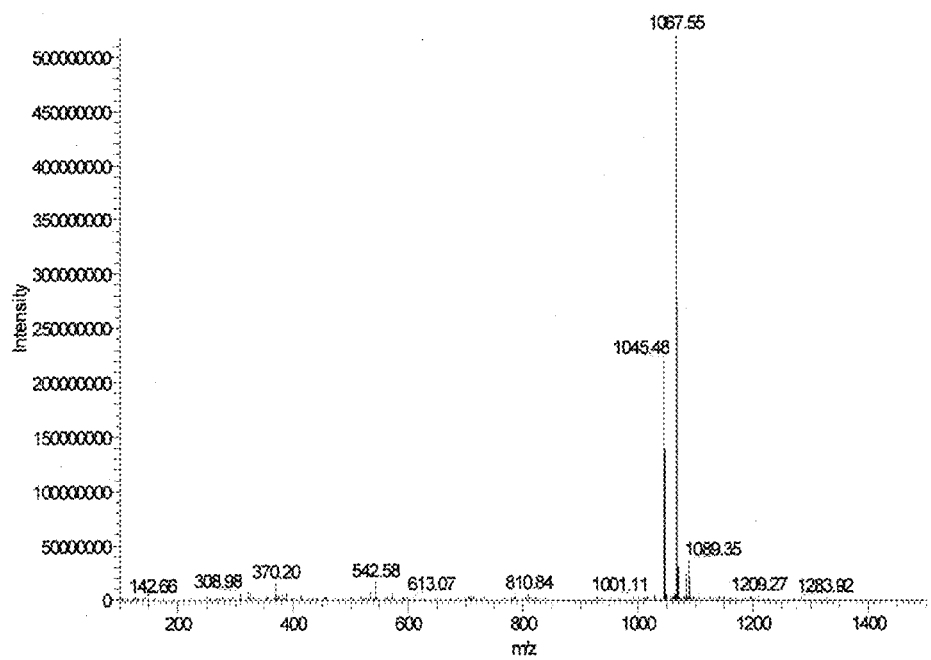
FIG. 3 depicts the (+) ESIMS for compound "A".

The molecular weight of Compound A (F727F3H11) was determined to be 1044, based on a molecular ion peak at 1043.84 (M−H) in the negative ionization mode (FIG. 2). This determination was supported by the ionization pattern in the positive mode ESIMS, which showed a peak at 1045.48 (M+H) and a pseudomolecular ion peak at 1067.55 (M+Na) (FIG. 3).

Figure 4:
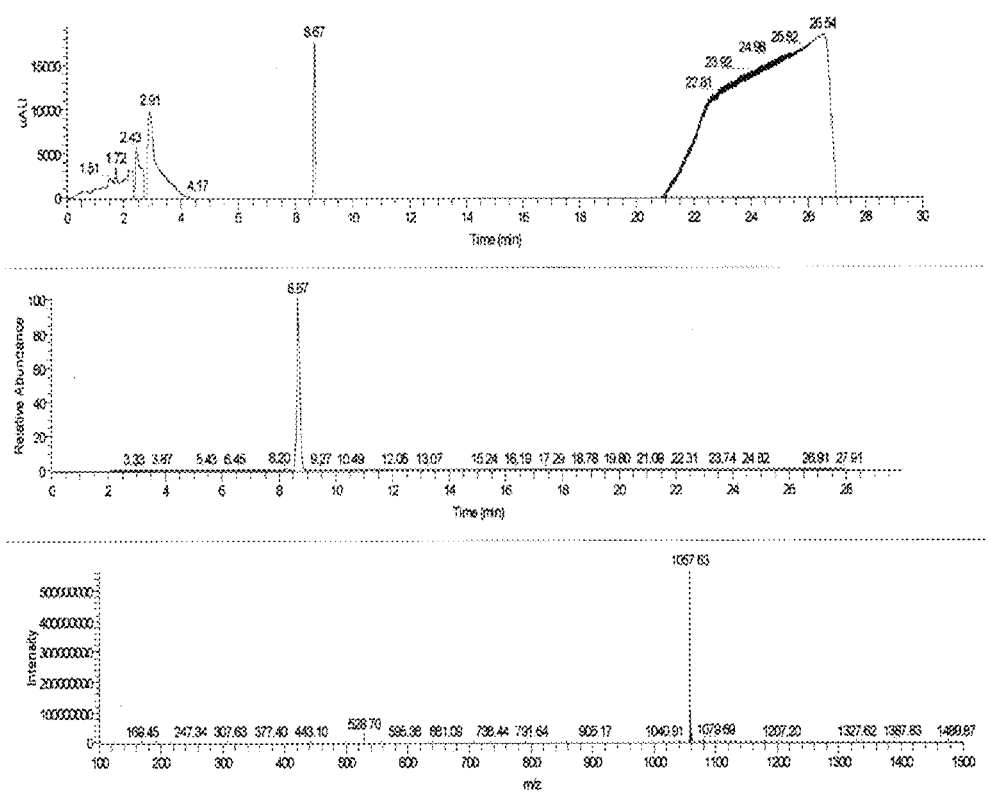
FIG. 4 depicts the ESI-LCMS chromatogram for compound "B".
Figure 5:
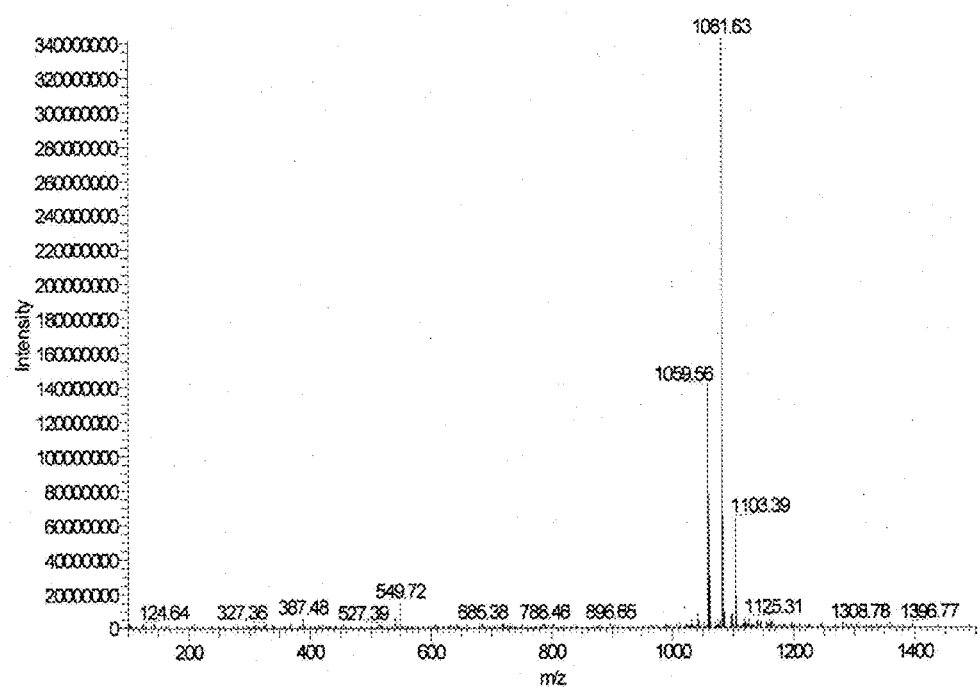
FIG. 5 depicts the (+) ESIMS for compound "B".

The molecular weight of Compound B (F727F3H14) was determined to be 1058, based on a molecular ion peak at 1057.83 (M−H) in the negative ionization mode (FIG. 4). This determination was supported by the ionization pattern in the positive mode ESIMS which showed a peak at 1059.56 (M+H) and a pseudomolecular ion peak at 1081.63 (M+Na) (FIG. 5).

Figure 6:
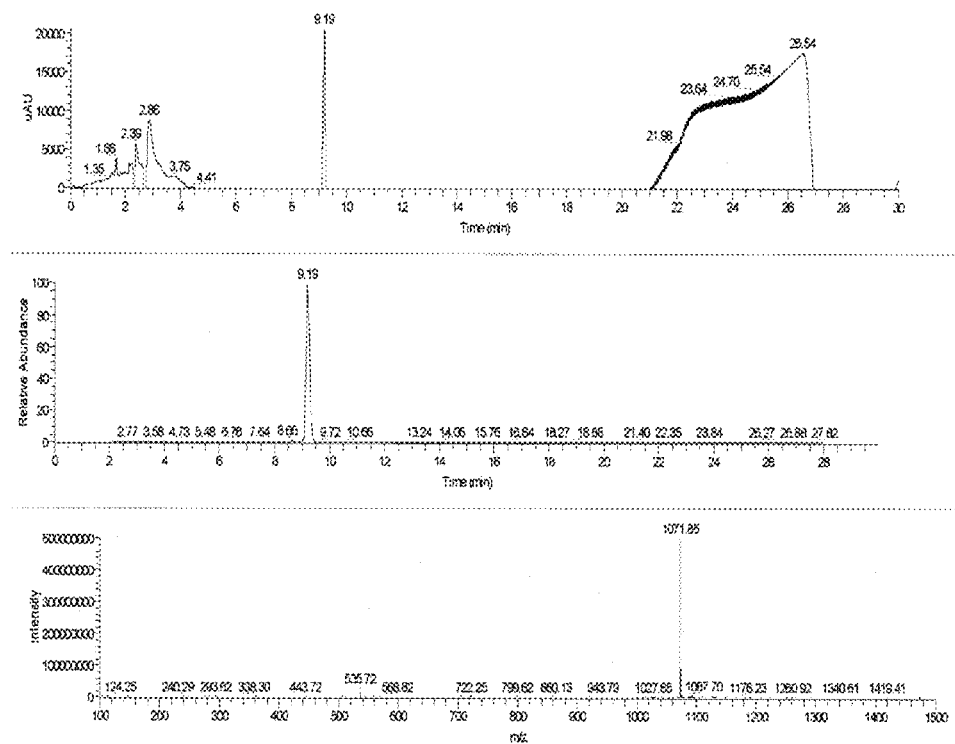
FIG. 6 depicts the ESI-LCMS chromatogram for compound "C".
Figure 7:
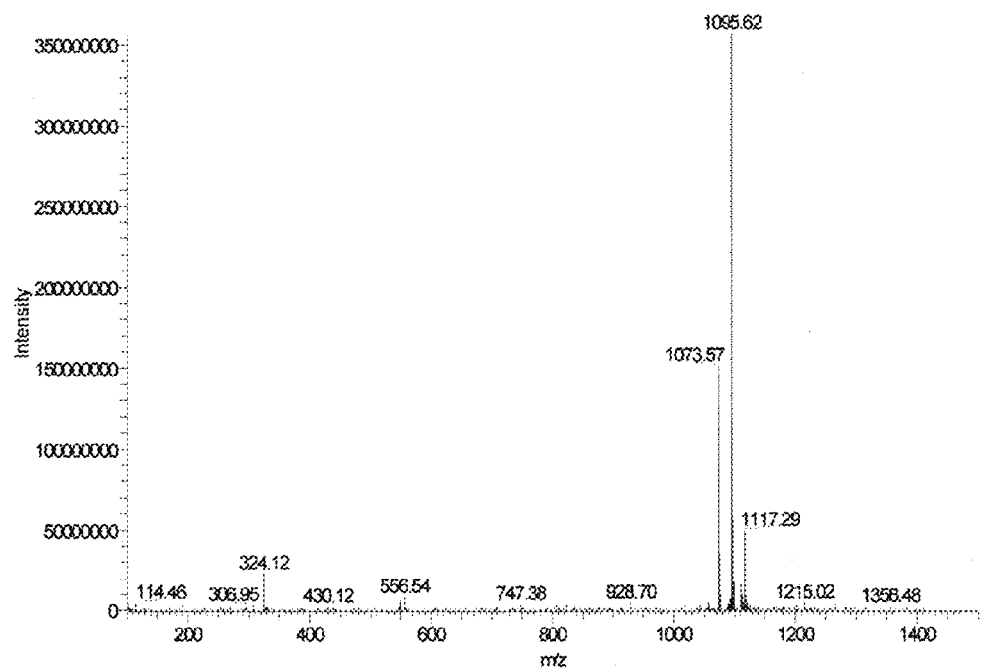
FIG. 7 depicts the (+) ESIMS for compound "C".

The molecular weight of Compound C (F727F3H17) was determined to be 1072, based on a molecular ion peak at 1071.85 (M−H) in the negative ionization mode (FIG. 6). This determination was supported by the ionization pattern in the positive ESIMS which showed a peak at 1073.57 (M+H) and a pseudomolecular ion peak at 1095.62 (M+Na) (FIG. 7).

Plug Assay Method for Antifungal Testing of Fraction and Pure Compounds

Figure 8:
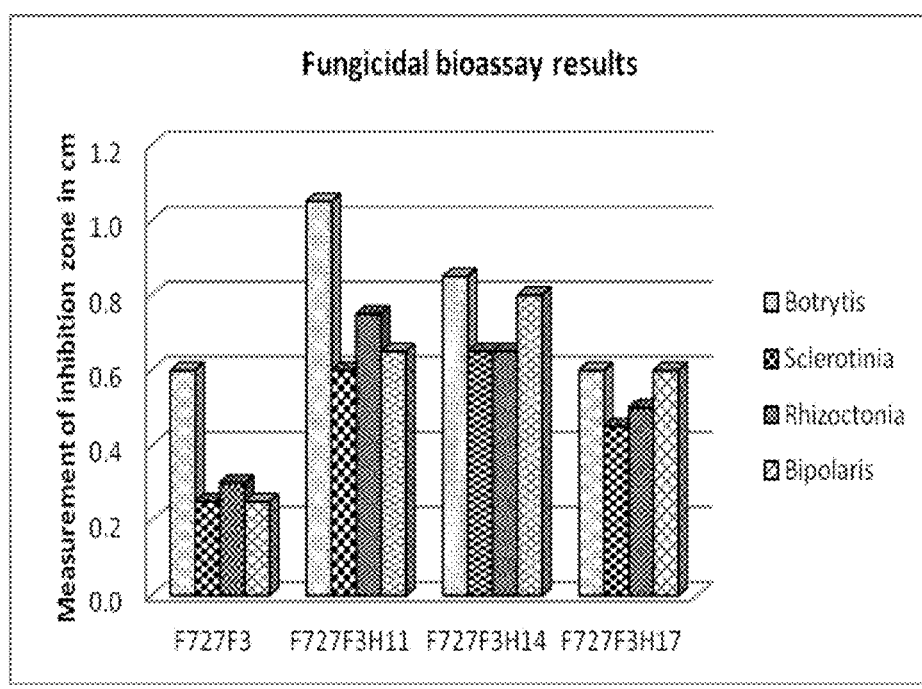
FIG. 8 depicts the bioactivity of VLC fraction 3 (F727F3 in Figure), and HPLC-purified Compound A (F727F3H11 in Figure), Compound B (F727F3H14 in Figure) and Compound C (F727F3H17 in figure) against four fungal pathogens: *Botrytis cinerea* (*Botrytis* in Figure), *Sclerotinia homeocarpa* (*Sclerotina* in Figure), *Rhizoctonia solani* (*Rhizoctonia* in Figure) and *Bipolaris maydis* (*Bipolaris* in Figure).

Fractions and purified compounds were tested for antifungal activity as follows. A filter disc was placed in each quadrant of a medium-sized petri dish (four discs total). Each disc was placed 2 cm from the center of the dish. 15 µL of column fraction or purified compound (20 mg/mL) was dispensed onto the surface of each of two discs opposite each other. Ethanol was dispensed on the other two discs as a control. After the filter discs were loaded, small plugs (ca. 1×1 cm) of fungi were placed in the center of the petri dish. Fungal pathogens used were *Bipolaris maydis, Botrytis cinerea, Sclerotinia homeocarpa* and *Rhizoctonia solani*. The plates were incubated at 25° C. and, after 48 hours, the zone of inhibition around each filter disc was measured. The results are shown in FIG. 8 for VLC fraction 3 and compounds A, B and C; and indicate that all three compounds possess significant fungicidal activity.

Amino Acids Analysis of Compounds A, B & C

Compound A (F727F3H11, 0.05 mg) was hydrolyzed by liquid phase hydrolysis (6N HCL, 1% Phenol, 110° C., 24 hr, in vacuum). After cooling, the reaction mixture was dried and the hydrolyzed product was dissolved in Norleu dilution buffer to 1.0 mL volume. A 50 µl aliquot of this sample was loaded onto an ion-exchange column for analysis.

For standards and calibration, an amino acid standards solution for protein hydrolysate on the Na-based Hitachi 8800 (Sigma, A-9906) was used to determine response factors, and thus calibrate the Hitachi 8800 analyzer for all of the amino acids. Each injection contained norleucine as an internal standard, to allow correction of the results for variations in sample volume and chromatography variables. The system utilized Pickering Na buffers, Pierce Sequanal grade HCl (hydrolysis), a Transgenomic Ion-Exchange column and an optimized method developed by Molecular Structure Facility (MSF), UC Davis. The individual amino acids present in each sample were reported. The amino acids present in compound A were found to be glutamine (1 unit), proline (1 unit), serine (1 unit), tyrosine (1 unit) and asparagine (3 units).

The amino acid compositions of compounds B and C were analyzed in similar fashion. Compounds B and C were found to have the same amino acids, in the same ratio, as did compound A.

Example 6

Effect of *Bacillus* sp. Isolate F727 on *Botrytis* in Tomato Plants

Figure 9:
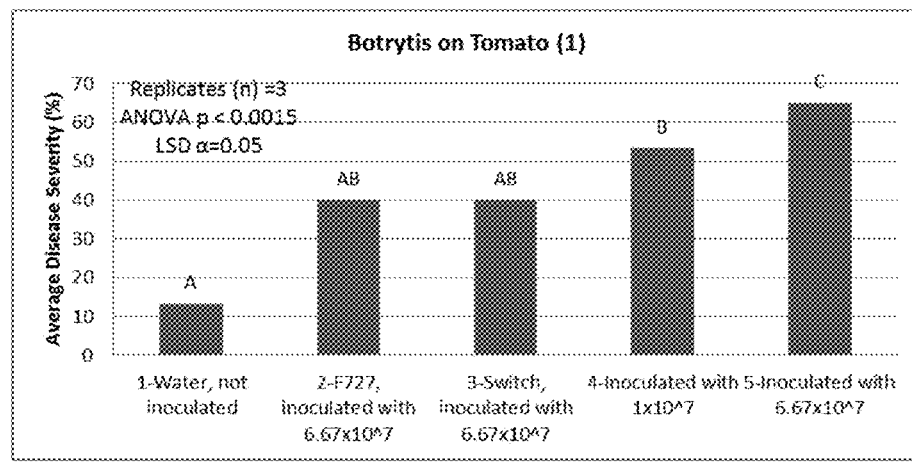
FIG. 9 shows the effect of F727 supernatant on *Botrytis cinerea* in tomato. Plants were inoculated with *B. cinerea* spores at the concentrations indicated in the Figure and were treated with supernatant from a *Bacillus* sp. F727 fermentation (second bar from left) or Switch® (third bar from left). Controls included non-inoculated plants (leftmost bar) and non-pesticide-treated plants inoculated with two different concentrations of the fungus (fourth and fifth bars from left).

Tomato plants (*Solanum lycopersicum*) var. Roma were treated with supernatant from an F727 fermentation. Each plant was sprayed with approximately 3 ml of cell-free fermentation supernatant. Plants were allowed to dry and were then inoculated with 2 ml of a suspension of *Botrytis cinerea* spores at a concentration of $6.67 \times 10^7$ spores/ml. A control plant was sprayed with deionized water, two negative control plants were sprayed only with spores (at concentrations of $1 \times 10^7$ spores/ml and $6.67 \times 10^7$ spores/ml), and a positive control plant was sprayed with SWITCH® 65.2 WG (Cypronidil and Fludioxonil, marketed by Bayer Crop Sciences, Inc.) at rate of 14 oz/100 gal/acre. Treatments were performed in triplicate. Plants were placed in a transparent plastic bin in a growth room with lights and constant temperature control. Disease rating was performed 8 days after treatment. Plants were evaluated for disease severity by visual evaluation of a leaf area symptomatic of the disease and a disease rating was obtained. See, for example, W C James (1971) "A Manual of Assessment Keys in Plant Diseases." American Phytopathological Society. ISBN 978-0-89054-081-7. The results, shown in FIG. 9, show that disease severity was reduced from 65% (infected, untreated control) to 40% in infected plants treated with F727 supernatant.

Example 7

Effect of *Bacillus* sp. F727 on Downey Mildew in Lettuce

Lettuce plants (*Lactuca sativa*) var. Celtuce, were planted at a density of four seedlings per pot. Each pot was sprayed with 2 ml F727 fermentation supernatant.

Plants were allowed to dry and then inoculated with 2 ml of a *Bremia lactuca* (downy mildew) spore suspension ($1 \times 10^5$ spores/ml). Treatments were performed in 5 replicates. Treated plants were incubated in trays sealed with a plastic cover, at 15° C. in a growth chamber with a 12 hour photoperiod. At 10 days after treatment, disease severity was evaluated as described in Example 6.

Figure 10:
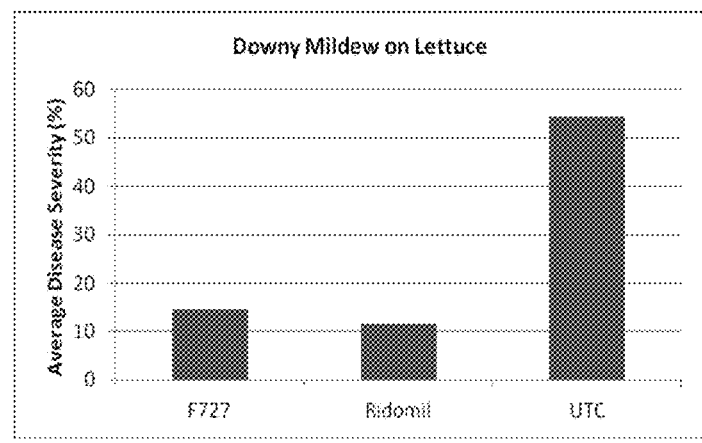
FIG. 10 shows the effect of F727 supernatant on Downy Mildew in lettuce. Plants were treated with *Bacillus* sp. isolate F727 supernatant (F727); Ridomil, or were untreated (UTC).

The results are shown in FIG. 10. Average disease severity in the untreated control was 54.47%, while plants treated with F727 showed a disease severity of only 14.64%. The disease severity in the F727 treated plants was comparable to that obtained after treatment of plants with the chemical control RIDOMIL® GOLD EC (4% w/w metalaxyl-M and 64% w/w mancozeb) (150 ppm a.i.) (Syngenta), which provided 11.67% severity.

Example 8

Comparison of the Effect of *Bacillus* sp. F727 with ELEVATE

Tomato plants (*Solanum lycopersicum*) var. Roma were treated with 3 ml F727 fermentation supernatant and allowed to dry. Plants were then inoculated with approximately 2 ml *Botrytis cinerea* spore suspension ($2.8 \times 10^7$ spores/ml). A subset of the infected plants was spayed a second time with F727, after 2 hours or after the first treatment was dry. Inoculated plants were also treated with water (negative control) and ELEVATE® 50 WDG (Fenhexamid, Bayer Crop Science, Inc.) as a positive control.

Figure 11:
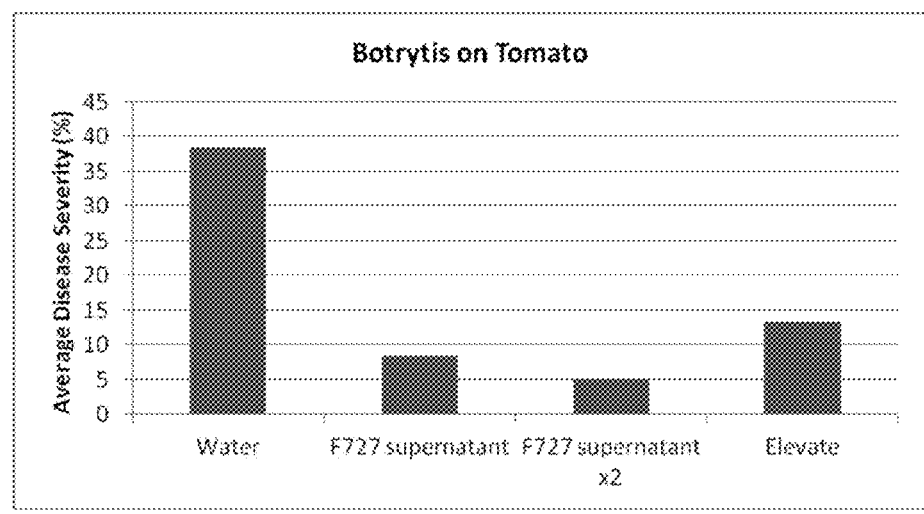
FIG. 11 compares effect of F727 supernatant with Fenhexamid on *Botrytis* in tomato. Plants that had been experimentally infected with *B. cinerea* were pre-sprayed either once (F727 supernatant) or twice (F727 supernatant×2) with F727 supernatant, with water or with Fenhexamid (Elevate®), and disease severity was assayed.

Treatments were performed in replicates of 4. Nine days after treatment, disease severity was evaluated as described in Example 6. The results are shown in FIG. 11. Disease severity for the water control was 38.3%, while the positive control (ELEVATE® 50 WDG, Fenhexamid, Bayer Crop Science, Inc.) reduced disease severity to 13.33%. Plants treated with 1× and 2× F727 supernatant had a disease severity of 8.3 and 5% respectively.

Example 9

Effect of F727 Supernatant on *B. cinerea* Infection in Peppers

Pepper plants (*Capsicum annuum*) var. Serrano were sprayed with approximately 2 ml F727 supernatant and allowed to dry. Plants were then inoculated with 2 ml of a spore suspension of *Botrytis cinerea* ($2.7 \times 10^7$ spores/ml). Plants were treated in triplicate. Thirteen days after treatment, disease severity was evaluated and compared to an untreated control (sprayed with water) and a positive control (sprayed with Elevate® 50 WDG (Fenhexamid, Bayer Crop Science, Inc.) applied at label rate.

Figure 12:
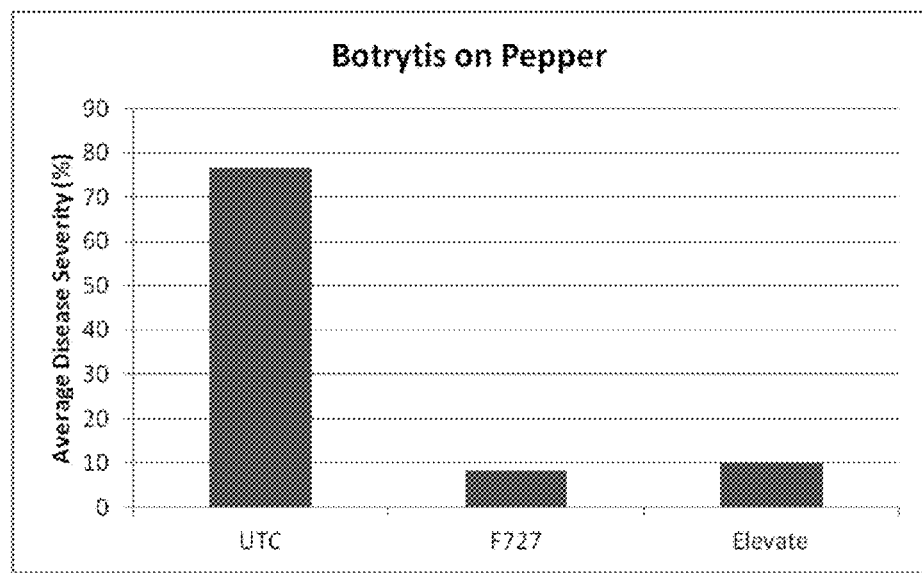
FIG. 12 compares effect of F727 supernatant with Fenhexamid on *Botrytis* in peppers. Plants were sprayed with supernatant from a *Bacillus* sp. isolate F727 fermentation (F727), water, (UTC) or Fenhexamid (Elevate®). Sprayed plants were then experimentally infected with *B. cinerea*, grown, and assayed after 13 days for disease severity.

The results, shown in FIG. 12, indicate that disease control in *Botrytis cinerea*-infected plants that had been treated with F727 was comparable to that obtained by treatment of plants with Elevate®.

Example 10

Evaluation of F727 Whole Cell Broth, Supernatant and Cells Produced by Fermentation in Three Media Against Powdery Mildew on Cucumber F727 cells were fermented in three different growth media (SPY, SMP and TSB). Two week-old cucumber plants (*Cucumis sativus*) var. SMR58 were sprayed with approximately 3 mL of F727 whole-cell broth, F727 supernatant or F727 cells obtained from each of these three fermentations. Cells were pelleted, then resuspended in 10 mM magnesium sulfate for spraying. Four replicates per treatment were conducted. Plants were allowed to dry for two hours before being sprayed with approximately 2 mL of a powdery mildew spore suspension at a concentration of $3.0 \times 10^5$ spores/mL, that had been prepared from an infected plant. Plants were then incubated in a growth room until disease development, and disease severity was evaluated as described in Example 6.

Figure 13:
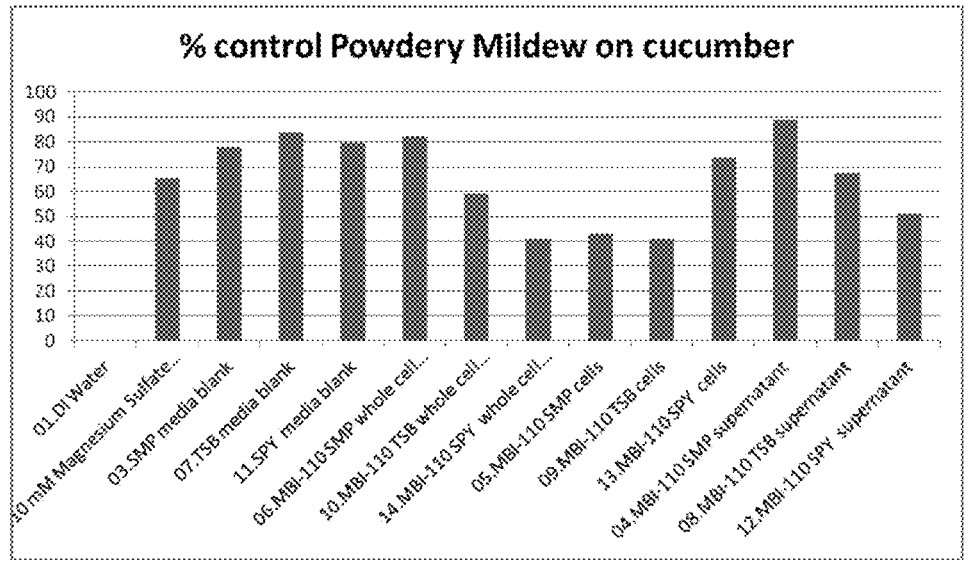
FIG. 13 shows measurements of disease control on cucumbers infected with powdery mildew and treated with different F727 preparations. F727 cells were grown in three different media: SPY, SMP and TSB, as indicated in the figure. Whole cell broth, cells (suspended in 10 mM $MgSO_4$), and supernatant were obtained for each of these growth conditions. Water ("DI Water" in the figure) was used as a negative control. Blanks for SMP medium, SPY medium, TSB medium and 10 mM $MgSO_4$ were also included.

The results, expressed as percentage disease control, are shown in FIG. 13. Anti-fungal activity on cucumber was observed with whole cells, whole-cell broth and cell supernatants obtained from all three media.

Example 11

Evaluation of Efficacy of F727 Whole Cell Broth, Supernatant and Cells Produced by Fermentation in Three Media Against *Botrytis cinerea* on Tomato Two week old tomato plants (*Solanum lycopersicum*) var. Stupice were sprayed with approximately 2 mL of F727 whole-cell broth, F727 supernatant and F727 cells, each prepared from three separate fermentations in different growth media (SPY, SMP and TSB). Cells were pelleted and resuspended in 10 mM magnesium sulfate for spraying. Three replicates per treatment were conducted. Plants were allowed to dry for one hour, then placed under humid conditions to open stomata. Approximately 1 mL of a *Botrytis cinerea* spore suspension prepared from a ten-day old cultured agar plate at $1.0 \times 10^7$ spores/mL in 2% Sabouraud maltose broth was sprayed on each plant. Plants were incubated in a growth chamber with a 12 hour photoperiod until disease development, and disease severity was evaluated as described in Example 6.

Figure 14:
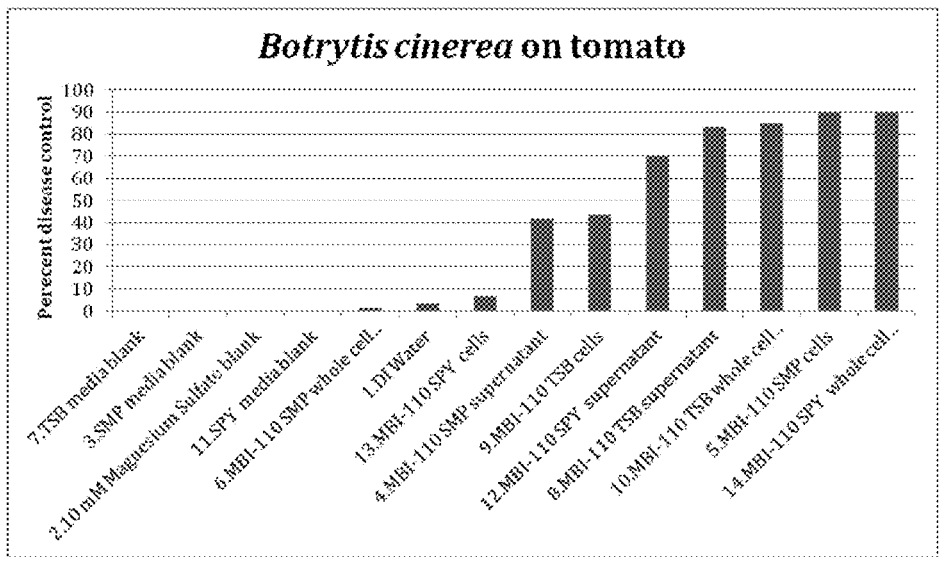
FIG. 14 shows measurements of disease control on tomato plants infected with *Botrytis cinerea* and treated with different F727 preparations. F727 cells were grown in three different media: SPY, SMP and TSB, as indicated in the figure. Whole cell broth, cells (suspended in 10 mM $MgSO_4$), and supernatant were obtained for each of these growth conditions. Water ("DI Water" in the figure) was used as a negative control. Blanks for SMP medium, SPY medium, TSB medium and 10 mM $MgSO_4$ were also included.

The results, expressed as percentage disease control, are shown in FIG. 14. Anti-fungal activity on tomato was observed with whole cells, whole-cell broth and cell supernatants obtained from all three media.

Example 12

Evaluation of Efficacy of F727 Whole Cell Broth, Commercial *Bacillus*-Based Products and F727 Whole Cell Broth Mixed with Regalia® Against Powdery Mildew on Cucumber Two week old cucumber plants (*Cucumis sativus*) var. SMR58 were sprayed at first true leaf with approximately 3 mL of: Regalia® 5% (*Renoutria sachalinensis*, Marrone Bio Innovation, Inc., Davis, Calif.) at 1:2000, Regalia® 5% at 1:200, F727 whole cell broth, F727 whole cell broth+Regalia® 5% at 1:2000, Serenade® (Bayer Crop Science, Inc.) at 1:200, Sonata® (Bayer Crop Science, Inc.) at 1:200, Vacciplant® (Laboratoires Goemar S.A.) at 40 µL/50 mL, Companion® (Growth Products, Ltd.) at 1:200, and Double Nickel 55® (Certis USA, L.L.C.) at 0.06 g/50 mL. Four replicates per treatment were prepared. Plants were allowed to dry for two hours before approximately 2 mL of a powdery mildew spore suspension at a concentration of $3.0 \times 10^5$ spores/mL was sprayed on each plant. Plants were incubated in a growth room until disease development.

Figure 15:
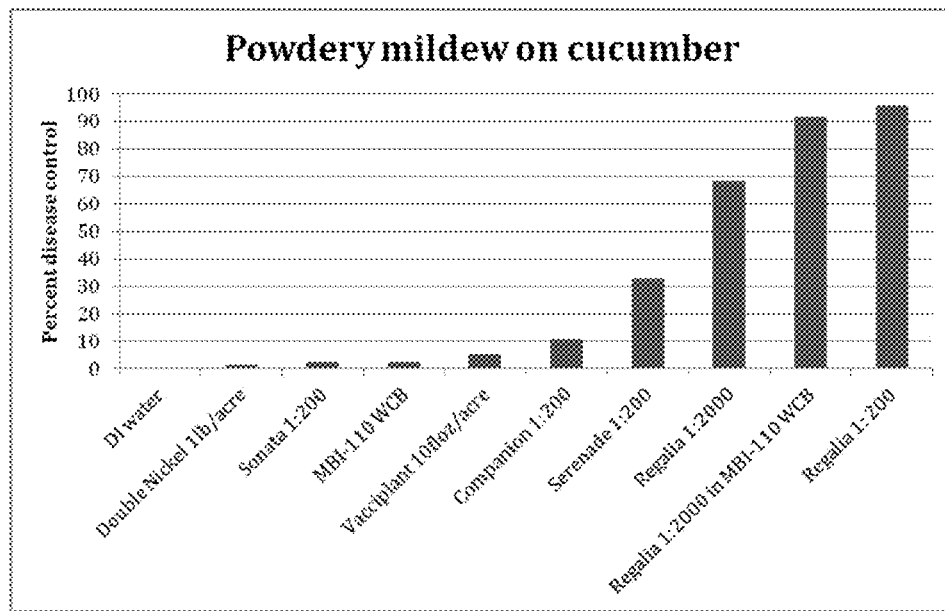
FIG. 15 shows measurements of disease control in cucumber plants infected with powdery mildew. Prior to inoculation with fungal spores, plants were sprayed with water ("DI water" in figure, negative control), whole cell broth from isolate F727 fermentation (MBI-110 WCB) or one of a number of commercial pesticides (Double Nickel® (Certis, *Bacillus amyloliquefaciens* strain D747) Sonata® (*Bacillus subtilus*), Vacciplant®, Companion®, Serenade® (*Bacillus pumilus*) or Regalia® (*Reynoutria sachalinensis*), or a combination of Regalia® (*Reynoutria sachalinensis*) and F727 WCB.

The results, shown in FIG. 15, indicate that whole cell broth from a *Bacillus* sp. isolate F727 fermentation (identified as MBI-110 WCB in the Figure) is more effective against powdery mildew that many existing fungicides. Results for Regalia® with and without F727 supernatant are shown in Table 6. Colby's synergy coefficient indicates that synergy exists between F727 whole cell broth and Regalia® 5% at 1:2000.

TABLE 6

| Treatment | Mean Severity | % Control | Colby Expected | Colby Synergy Coefficient |
|---|---|---|---|---|
| F727 WCB | 92.5 | 2.6 | — | — |
| Regalia 1:2000 (v/v) | 30 | 68.4 | — | — |
| Regalia 1:2000 9v/v) in F727 WCB | 8 | 91.6 | 69.3 | 1.32 |

Example 13

Evaluation of Efficacy of F727 Whole Cell Broth, Regalia® and Double Nickel 55® Against *Phytophthora infestans* on Tomato Tomato plants (*Solanum lycopersicum*) var. Stupice at a two true leaf stage were sprayed with 2 mL of F727 whole cell broth, Regalia® at 1:200 (Marrone Bio Innovations, Inc.) and Double Nickel 55® at 0.06 g/50 mL (Certis USA, L.L.C.). Plants were allowed to dry before being sprayed to coverage with a solution of *Phytophthora infestans* spores, at a concentration of $10^4$ spores/mL, prepared from infected tomato leaves. Plants were incubated in a 20° C. growth chamber under artificial light. Three days after treatment, the plants were assessed for disease severity as described in Example 6.

Figure 16:
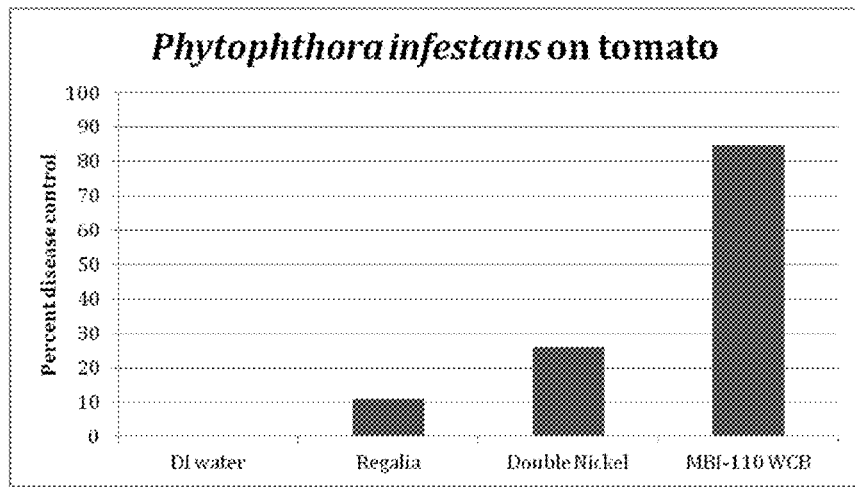
FIG. 16 shows measurements of disease control in tomato plants infected with *Phytophthora infestans*. Prior to inoculation with *P. infestans*, plants were sprayed with water ("DI water" in figure, negative control), Regalia®, Double Nickel® (Certis, *Bacillus amyloliquefaciens* strain D747) or whole cell broth from isolate F727 fermentation (MBI-110 WCB).

The results, shown in FIG. 16, indicate that whole cell broth from a *Bacillus* sp. isolate F727 fermentation (identified as MBI-110 WCB in the Figure) provides robust protection against *P. infestans* infection of tomatoes.

Example 14

Evaluation of F727 Control of *Sclerotium rolfsii* In Vitro

Isolate F727 was fermented in liquid medium and the supernatant was removed by centrifugation. Half of the supernatant was filtered through a 0.2 µm filter. Single sclerotia of *Sclerotium rolfsii* were placed in the centers of 10 cm petri plates and four 0.5 cm diameter discs per plate were placed at a distance of 2 cm from the fungus and at equal distances from each other. F727 supernatant, filtered F727 supernatant and Pristine® (BASF) at 0.5 mL/L were added to the discs in 12.5 µl aliquots, until the until two opposing disks held a total of 25 µl and the other two held 50 µl. Two plates per treatment were prepared. Plates were incubated at 25° C. for three days.

Figure 17:
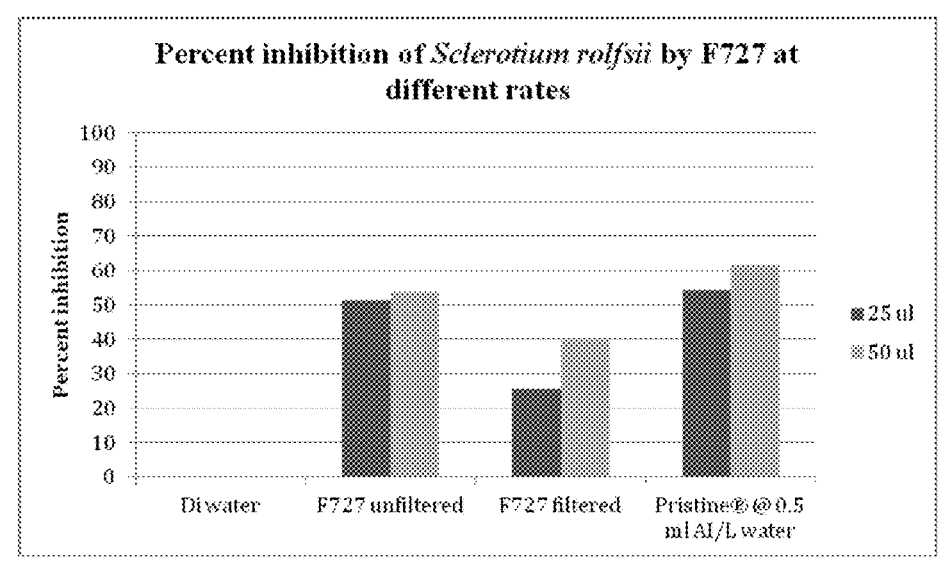

The percent inhibition for each test substance was determined by measuring the mycelial growth from the sclerotium to the furthest edge of the colony toward each disk. Results, shown in FIG. 17, indicate that both filtered and unfiltered supernatants of F727 were effective in inhibiting the growth of *S. rolfsii* in the disc assay. The unfiltered supernatant was consistently more effective than the filtered and its effectiveness was comparable to that of the commercial standard.

Example 15

Evaluation of F727 Control of *Rhizoctonia solani* on Soybean

Sterile barley grains were inoculated with *Rhizoctonia solani* and incubated for 1-2 weeks. The grains were dried, blended and mixed with sand at a one-to-one ratio to generate a *R. solani* inoculum. Soil was thoroughly mixed with this inoculum to a volume of 500 mL of soil per pot, watered with 100 mL of water and incubated in a growth room for 24 hours. Isolate F727 whole cell broth was prepared at 100%, 50% and 25% strength. The soil was then drenched with 40 mL of each broth dilution, and nine soybean seeds were planted in each pot. For each replicate, there were three pots, and there were three replicates per treatment. Plants were incubated in a growth room for 14 days. Germination, plant height, fresh shoot weight and fresh root weight were evaluated.

Measurements of shoot stands (Table 7), emergence (Table 8), average shoot weight (Table 9) and mean shoot height (Table 10) were determined. The results indicate that F727 whole cell broth increased emergence, shoot weight and shoot height in *R. solani*-infected soybean plants.

TABLE 7

| Treatment | N | Stands (Mean of 3 reps) | StDev | Fisher Grouping |
|---|---|---|---|---|
| 1—Non-inoculated control; water treated | 3 | 24.7 | 1.16 | A |
| 2—Non-inoculated control; 100% F727 whole cell broth | 3 | 25.0 | 1.00 | A |
| 3—1:1600 inoc rate; 100% F727 whole cell broth | 3 | 11.0 | 3.61 | B |
| 4—1:1600 inoc rate; 50% F727 whole cell broth | 3 | 11.7 | 2.52 | B |
| 5—1:1600 inoc rate; 25% F727 whole cell broth | 3 | 8.0 | 3.61 | B |
| 6—1:1600 inoc rate; water control | 3 | 12.0 | 1.00 | B |
| | | ANOVA $p < 0.0005$ | | LSD $\alpha = 0.05$ |

TABLE 8

| Treatment | N | Emergence (Mean of 3 reps) | StDev | Fisher Grouping |
|---|---|---|---|---|
| 1—Non-inoculated control; water treated | 3 | 24.7 | 1.16 | A |
| 2—Non-inoculated control; 100% F727 WCB | 3 | 25.0 | 1.00 | A |
| 3—1:1600 inoc rate; 100% F727 whole cell broth | 3 | 18.0 | 2.65 | B |
| 4—1:1600 inoc rate; 50% F727 whole cell broth | 3 | 18.3 | 1.16 | B |
| 5—1:1600 inoc rate; 25% F727 whole cell broth | 3 | 14.7 | 3.21 | B |
| 6—1:1600 inoc rate; water control | 3 | 15.3 | 1.16 | B |
| | | ANOVA $p < 0.0005$ | | LSD $\alpha = 0.05$ |

TABLE 9

| Treatment | N | Average Shoot Weight (g) (Mean of 3 replicates) | StDev | Fisher Grouping |
|---|---|---|---|---|
| 1—Non-inoculated control; water treated | 3 | 22.4 | 0.87 | A |
| 2—Non-inoculated control; 100% F727 WCB | 3 | 24.8 | 2.09 | A |
| 3—1:1600 inoc rate; 100% F727 WCB | 3 | 11.2 | 3.23 | B |
| 4—1:1600 inoc rate; 50% F727 WCB | 3 | 12.0 | 1.71 | B |
| 5—1:1600 inoc rate; 25% F727 WCB | 3 | 8.9 | 2.88 | B |
| 6—1:1600 inoc rate; water control | 3 | 10.5 | 1.21 | B |
| | | ANOVA $p < 0.0005$ | | LSD $\alpha = 0.05$ |

TABLE 10

| Treatment | N | Shoot Height (cm) (Mean of 3 replicates) | StDev | Fisher Grouping |
|---|---|---|---|---|
| 1—Non-inoculated control; water treated | 74 | 13.1 | 3.27 | A |
| 2—Non-inoculated control; 100% F727 WCB | 75 | 14.0 | 3.132 | A |
| 3—1:1600 inoc rate; 100% F727 WCB | 54 | 7.9 | 3.641 | B |
| 4—1:1600 inoc rate; 50% F727 WCB | 55 | 7.3 | 5.052 | B C |
| 5—1:1600 inoc rate; 25% F727 WCB | 44 | 6.1 | 5.52 | C |
| 6—1:1600 inoc rate; water control | 46 | 6.0 | 5.144 | C |
| | | ANOVA $p < 0.0005$ | | LSD $\alpha = 0.05$ |

Example 16

Evaluation of F727 Control of Bacterial Plant Pathogens In Vitro

One ml of sterile water was inoculated with a loop of each of the bacterial plant pathogens, *Erwinia amylovora, Pseudomonas syringae, Bacillus cereus, Erwinia carotovora, Xanthomonas campestris, Xanthomonas arboricola* or *Clavibacter michiganensis* subsp. *michiganensis*, from cultured potato dextrose agar (PDA) plates. The bacteria were re-suspended and 100 µL of the pathogen re-suspension was streaked onto a PDA agar plate and left to be absorbed into the plate for 10-15 minutes. Sterile filter discs were applied to the agar and were loaded with 20 µL of F727 VLC fractions (10 mg/mL in methanol) or combinations of the VLC fractions. Fractions were obtained from a fermentation of *Bacillus* sp. isolate F727 in V8 medium. See Example 5, above.

Plates were incubated 24-48 hours and then inspected for the appearance of a zone of inhibition around the filter disc, indicating susceptibility of the pathogen to the F727 fraction. Results are shown in Table 11.

ment mix. The plates were incubated at 25° C. for 3-5 days, and visual evaluation of fungal spore germination was conducted.

The results are shown in Table 13. All supernatants tested inhibited the germination of all the pathogens at the lowest concentration tested (3.13%). The activity of the crude extracts varied depending on the media used to grow the F727 cells (a 0.4% dilution of crude extract was the lowest concentration tested). This indicated that the activity of F727 extracts can depend on the medium in which the cells are grown and, thus, optimal activity against a particular pathogen can be adjusted based on the medium in which the cells are grown. For example, M24 medium can be used to grow cells whose extracts would target *Fusarium*.

TABLE 12

| Pathogen | Spore concentration used |
| --- | --- |
| *Fusarium oxysporum* f. sp. *fragariae* | $10^4$ spores/mL |
| *Botrytis cinerea* | $10^4$ spore/mL |

TABLE 11

Susceptibility of bacterial phytopathogens to F727 fractions

| F727 sample | *Erwinia amylovora* | *Pseudomonas syringae* | *Bacillus cereus* | *Erwinia carotovora* | *Xanthomonas campestris* | *Xanthomonas arboricola* | *Clavibacter michiganensis* sub sp. *michiganensis* |
| --- | --- | --- | --- | --- | --- | --- | --- |
| 1. F727-F1 | − | + | − | − | − | + | + |
| 2. F727-F2 | ++ | − | − | − | + | − | ++ |
| 3. F727-F3 | ++ | + | − | − | + | + | + |
| 4. F727-F4 | ++ | + | − | + | − | − | − |
| 5. F727-F5 | + | − | +++ | +++ | − | + | +++ |
| 6. F727-F6 | + | − | + | − | − | − | + |
| 7. F727-F2 + F3 | − | − | − | + | − | + | ++ |
| 8. F727-F3 + F5 | − | − | + | ++ | − | − | +++ |
| 9. F727-F2 + F6 | − | − | − | − | − | − | + |
| 10. F727-F4 + F5 | + | − | ++ | +++ | − | − | +++ |
| 11. F727-F4 + F6 | − | − | ++ | − | − | − | − |
| 12. F727-F5 + F6 | − | − | +++ | + | − | − | ++ |

Key:
+++ very susceptible,
++ susceptible,
− resistant

Inhibition of the greatest number of bacterial species was observed with Fraction 3. Accordingly, this fraction was subjected to further fractionation, as described in Example 5, above. Additionally, Fraction 5 displayed antibacterial activity against *Bacillus cereus, Erwinia carotovora* and *Clavibacter*.

Example 17

Evaluation of F727 Supernatant and Crude Extract, Prepared in Different Media, for Control of Fungal Pathogen Germination In Vitro Isolate F727 was fermented in 12 different liquid media. Supernatant and crude extract samples were tested in a dose-response spore germination assay. In a 48-well plate, 100 µL of supernatant or crude extract sample was combined with 200 µL of 1.5× potato dextrose agar (PDA) and allowed to solidify. Spore suspensions from fungal plant pathogens were prepared at the concentrations shown in Table 12, and 50 µL of spore suspension was dispensed on top of the PDA/treat- TABLE 12-continued

| Pathogen | Spore concentration used |
| --- | --- |
| *Verticillium dahliae* | $10^5$ spores/mL |
| *Alternaria japonica* | $10^4$ spores/mL |

TABLE 13

Minimum inhibitory concentration of F727 crude extract from different media needed to prevent fungal spore germination

| Medium | *Botrytis cinerea* | *Fusarium oxysporum* f. sp. *fragariae* | *Verticillium dahliae* | *Alternaria japonica* |
| --- | --- | --- | --- | --- |
| M1 | 0.40% | 1.56% | 0.40% | 0.40% |
| M2 | 1.56% | 3.13% | 1.56% | 0.78% |
| M3 | 0.40% | 0.78% | 0.40% | 0.40% |
| M4 | 0.40% | 0.78% | 0.40% | 0.40% |
| M5 | 1.56% | No inhibition | 3.13% | 0.40% |
| M6 | 6.25% | No inhibition | 6.25% | 3.13% |
| M7 | 25.00% | No inhibition | 12.50% | 0.78% |

TABLE 13-continued

Minimum inhibitory concentration of F727 crude extract from different media needed to prevent fungal spore germination

| Medium | Botrytis cinerea | Fusarium oxysporum f. sp. fragariae | Verticillium dahliae | Alternaria japonica |
|---|---|---|---|---|
| M8 | No inhibition | No inhibition | 50.00% | No inhibition |
| M11 | 0.40% | 1.56% | 0.40% | 0.40% |
| M12 | 0.40% | 3.13% | 0.40% | 0.40% |
| M23 | 0.40% | 1.56% | 0.40% | 0.40% |
| M24 | 0.40% | 0.40% | 0.40% | 0.40% |

Example 18

Evaluation of Plant Growth Characteristics of F727 In Vitro

Isolate F727 was evaluated for plant growth characteristics in vitro, including the ability to solubilize phosphate, production of ACC-deaminase, production of indole-3-acetic acid (IAA), production of siderophores (CAS agar) and the ability to grow with methanol as the sole carbon source (AMS agar). Phosphate solubilization was evaluated in bromophenol blue-phosphate agar, ACC-deaminase activity was evaluated on agar plates with ACC as sole carbon and nitrogen source, siderophore production was evaluated on CAS agar, and methylotrophy was evaluated on a mineral salts agar amended with methanol as the only carbon source. As shown in Table 14, Isolate F727 tested positive for all of these plant growth promotion traits.

TABLE 14

| | Phosphate solubilization | ACC-deaminase | IAA | CAS agar | AMS agar |
|---|---|---|---|---|---|
| F727 | +++ | +++ | + | ++ | ++ |

Key:
+++: very strong positive response,
++: positive response,
+: weak positive response

Example 19

Vigor Analysis of Seeds Treated with F727

Corn, soy, wheat, rice, sorghum and tomato seeds were surface sterilized for six minutes with 1% bleach and rinsed with sterile water five times. Seeds were submerged for 24 hours in F727 suspension prepared in 10 mM magnesium sulfate. The seeds were dried for 30 minutes for Experiment #1 and overnight for Experiment #2. Seeds were allowed to germinate in moist paper towels for several days, and total fresh weight of the seeds was measured.

The results are shown in Table 15, and indicate that Bacillus sp. isolate F727 cells promoted growth of corn, soybean, sorghum and tomato.

TABLE 15

| | Experiment #1 Total fresh weight (grams) | | | Experiment #2 Total fresh weight (grams) | |
|---|---|---|---|---|---|
| | Control | F727 | | Control | F727 |
| Corn# | 14.06 | 13.81 | Corn* | 22.96 | 25.67 |
| Soy | 5.46 | 12.22 | Soy | 18.65 | 15.34 |
| Wheat | 3.83 | 3.61 | Wheat | 3.19 | 3.2 |
| Rice | 1.47 | 1.32 | Rice | 1.31 | 1.25 |
| Sorghum | 0.89 | 2 | Sorghum | 1.12 | 1.346 |
| Tomato | 0.38 | 0.58 | Tomato | 0.34 | 0.43 | var. Kandy Korn
*var. Trucker's Favorite Yellow, Boone County White and Silver King.

Example 20

Antifungal Activity Against Aspergillus niger

Whole cell broth (WCB) from a fermentation of Bacillus sp. isolate F727 was evaluated for its inhibitory effect on the post-harvest pathogen Aspergillus niger, in a fruit dip assay. WCB was used undiluted, and diluted in sterile water to concentrations of 5%, 20%, and 50%.

Sterilized green grapes were dipped for five seconds in each of the concentrations of WCB, then placed on a rack inside a crisper box. Once the fruit was dry, each box received 24 sprays of A. niger inoculum adjusted to $3 \times 10^3$ spore/ml. 100 ml of deionized water was added to each box underneath the rack to increase humidity, and the boxes were sealed and incubated at room temperature. Two crisper boxes, each containing 5 grapes per treatment, were included in the experiment. A water treatment was used as a negative control and the commercial product Switch was used as the positive control.

The percentage disease of each fruit was determined by observing mycelial coverage on each grape. The results are shown in Table 16, and indicate that F727 WCB exhibits significant anti-Aspergillis activity.

TABLE 16

Percent disease of A. niger on grapes after a dip treatment with F727 WCB after 12 days of growth.

| Treatment | Average % Disease | Grouping |
|---|---|---|
| Water | 71 | A |
| 5% WCB | 77.5 | A |
| 20% WCB | 34 | B |
| 50% WCB | 20.5 | BC |
| 100% B. WCB | 10 | C |
| Switch @ 14 oz/gal | 3.5 | C |

Example 21

Growth Promotion on Corn

Corn seeds were planted in potting soil mix, in pots with a diameter of 4 inches, at a density of 10 seed per pot. Seeded pots were drenched at planting time and one week thereafter with F727 whole cell broth. Pots were incubated in a greenhouse. A total of 10 plants per pot and 9 pots per treatment were evaluated.

Total fresh weight was recorded after 2 weeks' growth. Control plants (drenched with water) had a mean fresh weight of 21.48±4.02 g, while plants that had been drenched with F727 WCB had a mean fresh weight of 26.5±3.55 g. These differences are statistically significant, as determined by Minitab ANOVA Tukey's. These results provide additional evidence for the growth-promoting activity of F727 WCB.

Deposit of Biological Material

The following biological material has been deposited under the terms of the Budapest Treaty with the Agricultural Research Culture Collection (NRRL), 1815 N. University Street, Peoria, Ill. 61604 USA, and given the following number:

| Deposit | Accession Number | Deposit Date |
|---|---|---|
| *Bacillus* sp. strain F727 | NRRL B-50768 | Aug. 1, 2012 |

The strain has been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by government action.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. A composition comprising:
(a) a whole cell broth collected from *Bacillus* strain F727 (NRRL Accession No. B-50768) fermentation, wherein the *Bacillus* strain F727 has a nucleotide sequence having at least 95% identity to the recA sequence set forth in SEQ ID NO: 10, and pesticidal activity; and (b) at least one of a carrier, diluent, surfactant, or adjuvant.

2. The composition according to claim 1, further comprising a chemical or biological pesticide.

3. The composition of claim 1, wherein the *Bacillus* strain F727 is resistant to Kanamycin, Chloramphenicol, Ampicillin, Penicillin, Cefuroxime, Piperacillin or Tetracycline.

4. The composition of claim 1, wherein the *Bacillus* strain F727 possesses alkaline phosphatase, esterase, acid phosphatase, or naphthol-AS-BI-Phospho hydrolase activities.

5. A method for modulating a pest infestation in a plant comprising
   applying an amount of the composition of claim 1, sufficient to modulate said pest infestation to the plant and/or seeds thereof and/or substrate used for growing said plant wherein the composition optionally comprises an additional pesticide.

6. The method of claim 5, wherein the pest is a fungus or a bacterium.

7. The method of claim 6, wherein the fungus is selected from the group consisting of *Botrytis, Sclerotinia, Rhizoctonia,* and *Bipolaris*.

8. The method of claim 5, wherein the pest is a fungus and the pesticide is derived from *Reynoutria sachalinensis*.

9. A method for modulating the growth of a plant and/or germination of a seed comprising:
   contacting said plant, its growth substrate, and/or a seed of said plant with an amount of the composition of claim 1, and optionally with one or more substances effective to modulate growth of said plant and/or germination of said seed.

10. The method according to claim 9, wherein the one or more substances comprise a growth promoting agent, a surfactant, a carrier, an adjuvant, and/or a fertilizer.

11. A seed comprising the composition of claim 1.

* * * * *

SEQUENCE LISTING

```
<160> NUMBER OF SEQ ID NOS: 13

<210> SEQ ID NO 1
<211> LENGTH: 1250
<212> TYPE: DNA
<213> ORGANISM: Bacillus sp. strain F727 FD1 16S Sequence
<220> FEATURE:
<221> NAME/KEY: misc_feature
<222> LOCATION: (931)..(931)
<223> OTHER INFORMATION: n is a, c, g, or t
<220> FEATURE:
<221> NAME/KEY: misc_feature
<222> LOCATION: (944)..(944)
<223> OTHER INFORMATION: n is a, c, g, or t
<220> FEATURE:
<221> NAME/KEY: misc_feature
<222> LOCATION: (1003)..(1005)
<223> OTHER INFORMATION: n is a, c, g, or t
<220> FEATURE:
<221> NAME/KEY: misc_feature
<222> LOCATION: (1008)..(1008)
<223> OTHER INFORMATION: n is a, c, g, or t
<220> FEATURE:
<221> NAME/KEY: misc_feature
<222> LOCATION: (1015)..(1016)
<223> OTHER INFORMATION: n is a, c, g, or t
<220> FEATURE:
<221> NAME/KEY: misc_feature
<222> LOCATION: (1058)..(1058)
<223> OTHER INFORMATION: n is a, c, g, or t
<220> FEATURE:
<221> NAME/KEY: misc_feature
<222> LOCATION: (1069)..(1069)
<223> OTHER INFORMATION: n is a, c, g, or t
<220> FEATURE:
<221> NAME/KEY: misc_feature
<222> LOCATION: (1079)..(1079)
<223> OTHER INFORMATION: n is a, c, g, or t
<220> FEATURE:
<221> NAME/KEY: misc_feature
<222> LOCATION: (1093)..(1093)
<223> OTHER INFORMATION: n is a, c, g, or t
<220> FEATURE:
<221> NAME/KEY: misc_feature
<222> LOCATION: (1098)..(1110)
<223> OTHER INFORMATION: n is a, c, g, or t
<220> FEATURE:
<221> NAME/KEY: misc_feature
<222> LOCATION: (1117)..(1119)
<223> OTHER INFORMATION: n is a, c, g, or t
<220> FEATURE:
<221> NAME/KEY: misc_feature
<222> LOCATION: (1122)..(1122)
```

```
<223> OTHER INFORMATION: n is a, c, g, or t
<220> FEATURE:
<221> NAME/KEY: misc_feature
<222> LOCATION: (1124)..(1124)
<223> OTHER INFORMATION: n is a, c, g, or t
<220> FEATURE:
<221> NAME/KEY: misc_feature
<222> LOCATION: (1128)..(1130)
<223> OTHER INFORMATION: n is a, c, g, or t
<220> FEATURE:
<221> NAME/KEY: misc_feature
<222> LOCATION: (1135)..(1137)
<223> OTHER INFORMATION: n is a, c, g, or t
<220> FEATURE:
<221> NAME/KEY: misc_feature
<222> LOCATION: (1141)..(1141)
<223> OTHER INFORMATION: n is a, c, g, or t
<220> FEATURE:
<221> NAME/KEY: misc_feature
<222> LOCATION: (1144)..(1144)
<223> OTHER INFORMATION: n is a, c, g, or t
<220> FEATURE:
<221> NAME/KEY: misc_feature
<222> LOCATION: (1149)..(1150)
<223> OTHER INFORMATION: n is a, c, g, or t
<220> FEATURE:
<221> NAME/KEY: misc_feature
<222> LOCATION: (1152)..(1154)
<223> OTHER INFORMATION: n is a, c, g, or t
<220> FEATURE:
<221> NAME/KEY: misc_feature
<222> LOCATION: (1157)..(1157)
<223> OTHER INFORMATION: n is a, c, g, or t
<220> FEATURE:
<221> NAME/KEY: misc_feature
<222> LOCATION: (1159)..(1160)
<223> OTHER INFORMATION: n is a, c, g, or t
<220> FEATURE:
<221> NAME/KEY: misc_feature
<222> LOCATION: (1165)..(1168)
<223> OTHER INFORMATION: n is a, c, g, or t
<220> FEATURE:
<221> NAME/KEY: misc_feature
<222> LOCATION: (1173)..(1178)
<223> OTHER INFORMATION: n is a, c, g, or t
<220> FEATURE:
<221> NAME/KEY: misc_feature
<222> LOCATION: (1182)..(1182)
<223> OTHER INFORMATION: n is a, c, g, or t
<220> FEATURE:
<221> NAME/KEY: misc_feature
<222> LOCATION: (1185)..(1194)
<223> OTHER INFORMATION: n is a, c, g, or t
<220> FEATURE:
<221> NAME/KEY: misc_feature
<222> LOCATION: (1196)..(1197)
<223> OTHER INFORMATION: n is a, c, g, or t
<220> FEATURE:
<221> NAME/KEY: misc_feature
<222> LOCATION: (1199)..(1204)
<223> OTHER INFORMATION: n is a, c, g, or t
<220> FEATURE:
<221> NAME/KEY: misc_feature
<222> LOCATION: (1207)..(1208)
<223> OTHER INFORMATION: n is a, c, g, or t
<220> FEATURE:
<221> NAME/KEY: misc_feature
<222> LOCATION: (1210)..(1211)
<223> OTHER INFORMATION: n is a, c, g, or t
<220> FEATURE:
<221> NAME/KEY: misc_feature
<222> LOCATION: (1215)..(1215)
<223> OTHER INFORMATION: n is a, c, g, or t
<220> FEATURE:
<221> NAME/KEY: misc_feature
<222> LOCATION: (1217)..(1221)
<223> OTHER INFORMATION: n is a, c, g, or t
<220> FEATURE:
<221> NAME/KEY: misc_feature
```

```
<222> LOCATION: (1223)..(1228)
<223> OTHER INFORMATION: n is a, c, g, or t
<220> FEATURE:
<221> NAME/KEY: misc_feature
<222> LOCATION: (1232)..(1234)
<223> OTHER INFORMATION: n is a, c, g, or t
<220> FEATURE:
<221> NAME/KEY: misc_feature
<222> LOCATION: (1236)..(1238)
<223> OTHER INFORMATION: n is a, c, g, or t
<220> FEATURE:
<221> NAME/KEY: misc_feature
<222> LOCATION: (1240)..(1240)
<223> OTHER INFORMATION: n is a, c, g, or t
<220> FEATURE:
<221> NAME/KEY: misc_feature
<222> LOCATION: (1242)..(1245)
<223> OTHER INFORMATION: n is a, c, g, or t
<220> FEATURE:
<221> NAME/KEY: misc_feature
<222> LOCATION: (1247)..(1247)
<223> OTHER INFORMATION: n is a, c, g, or t
<220> FEATURE:
<221> NAME/KEY: misc_feature
<222> LOCATION: (1249)..(1250)
<223> OTHER INFORMATION: n is a, c, g, or t

<400> SEQUENCE: 1
tatacatgca agtcgagcgg acagatggga gcttgctccc tgatgttagc ggcggacggg      60
tgagtaacac gtgggtaacc tgcctgtaag actgggataa ctccgggaaa ccggggctaa     120
taccggatgc ttgtttgaac cgcatggttc aaacataaaa ggtggcttcg gctaccactt     180
acagatggac ccgcggcgca ttagctagtt ggtgaggtaa cggctcacca aggcaacgat     240
gcgtagccga cctgagaggg tgatcggcca cactgggact gagacacggc ccagactcct     300 acggaggca gcagtaggga atcttccgca atggacgaaa gtctgacgga gcaacgccgc     360
gtgagtgatg aaggttttcg gatcgtaaag ctctgttgtt agggaagaac aagtgccgtt     420
cgaatagggc ggcaccttga cggtacctaa ccagaaagcc acggctaact acgtgccagc     480
agccgcggta atacgtaggt ggcaagcgtt gtccggaatt attgggcgta aagggctcgc     540
aggcggtttc ttaagtctga tgtgaaagcc cccggctcaa ccggggaggg tcattggaaa     600
ctggggaact tgagtgcaga agaggagagt ggaattccac gtgtagcggt gaaatgcgta     660
gagatgtgga ggaacaccag tggcgaaggc gactctctgg tctgtaactg acgctgagga     720
gcgaaagcgt ggggagcgaa caggattaga taccctggta gtccacgccg taacgatgag     780
tgctaagtgt tagggggttt ccgcccctta gtgctgcagc taacgcatta agcactccgc     840
ctggggagta cggtcgcaag actgaaactc aaaggaattg acgggggccc gcacaagcgg     900
tggagcatgt ggtttaattc gaagcaacgc nagaacctta ccangtcttg acatcctctg     960
acaatcctag atataggacg tccccttcgg gggcagagtg acnnggngnc atggnngtcg    1020
tcagctcgtg tcgtgagatg ttgggtaagt cccgcacnag cgcaacccnt tgatcttant    1080
tgccagcatt canttggnnn nnnnnnnnnn actgccnnna cnanccgnnn aaggnnnggg    1140
natnacgtnn annnatncnn gccnnnntg acnnnnnca cnccnnnnnn nnnnanngnn      1200
nnnnaannan ngggncnnnn ngnnnnnnnaa annncnnncn cnnnngngnn             1250

<210> SEQ ID NO 2
<211> LENGTH: 1231
<212> TYPE: DNA
<213> ORGANISM: Bacillus sp. strain F727 RD1 16S Sequence

<400> SEQUENCE: 2
```

```
tcatctgtcc caccttcggc ggctggctcc ataaaggtta cctcaccgac ttcgggtgtt    60
acaaactctc gtggtgtgac gggcggtgtg tacaaggccc gggaacgtat tcaccgcggc   120
atgctgatcc gcgattacta gcgattccag cttcacgcag tcgagttgca gactgcgatc   180
cgaactgaga acagatttgt gggattggct taacctcgcg gtttcgctgc cctttgttct   240
gtccattgta gcacgtgtgt agcccaggtc ataagggca tgatgatttg acgtcatccc    300
caccttcctc cggtttgtca ccggcagtca ccttagagtg cccaactgaa tgctggcaac   360
taagatcaag ggttgcgctc gttgcgggac ttaacccaac atctcacgac acgagctgac   420
gacaaccatg caccacctgt cactctgccc ccgaagggga cgtcctatct ctaggattgt   480
cagaggatgt caagacctgg taaggttctt cgcgttgctt cgaattaaac cacatgctcc   540
accgcttgtg cgggccccg tcaattcctt tgagtttcag tcttgcgacc gtactcccca   600
ggcggagtgc tttaatgcgt tagctgcagc actaaggggc ggaaaccccc taacacttag   660
cactcatcgt tttacggcgt ggactaccag ggtatctaat cctgttcgct ccccacgct    720 ttcgctccct cagcgtcagt tacagaccca gagagtcgcc ttcgcccac tggtgttcct    780 ccacatcctc tacgcatttc acccggctac aacgtggaat ccactctcc tcttctgcac    840 tcaagtttcc ccagttttcca atgacccctc cccggttgag cccgggggct ttcacatcag   900
acttaaagaa acccgcctgc gagcccttta cgcccaataa ttccggacac gcttggccac   960
ctacgtatta ccgcgcttgc ttggcacgtt agtagccgtg gcttttctgg ttagttaacc  1020
gtcagtgccg cctattcgga acggtacttg ttcttcccta cacagagctt tacgatcgaa  1080
actcatcacc tccacgcgcg tgctcgtcag aactttcgtc atgcgaagat cctactgctg  1140
cctccgtagg gttggcgttt ctctcagtcc agtggccata cgtcagtagc tacccatcgt  1200
gcctagtgag cgttacctca cccacctagg c                                 1231

<210> SEQ ID NO 3
<211> LENGTH: 1459
<212> TYPE: DNA
<213> ORGANISM: Bacillus sp. strain F727 Consensus 16S Sequence

<400> SEQUENCE: 3
tatacatgca agtcgagcgg acagatggga gcttgctccc tgatgttagc ggcggacggg    60
tgagtaacac gtgggtaacc tgcctgtaag actgggataa ctccgggaaa ccggggctaa   120
taccggatgc ttgtttgaac cgcatggttc aaacataaaa ggtggcttcg gctaccactt   180
acagatggac ccgcggcgca ttagctagtt ggtgaggtaa cggctcacca aggcaacgat   240
gcgtagccga cctgagaggg tgatcggcca cactgggact gagacacggc ccagactcct   300
acgggaggca gcagtaggga atcttccgca atggacgaaa gtctgacgga gcaacgccgc   360
gtgagtgatg aaggttttcg gatcgtaaag ctctgttgtt agggaagaac aagtgccgtt   420
cgaatagggc ggcaccttga cggtacctaa ccagaaagcc acggctaact acgtgccagc   480
agccgcggta atacgtaggt ggccaagcgt tgtccggaat tattgggcgt aaagggctcg   540
caggcgggtt tctttaagtc tgatgtgaaa gcccccgggc tcaaccgggg agggtcatt    600 ggaaactggg gaacttgag tgcagaagag gagagtggaa ttccacgttg tagcggggtg   660
aaatgcgtag aggatgtgga ggaacaccag tggggcgaag gcgactctct gggtctgtaa   720
ctgacgctga gggagcgaaa gcgtggggga gcaacagga ttagataccc tggtagtcca   780
cgccgtaaaa cgatgagtgc taagtgttag ggggtttccg ccccttagtg ctgcagctaa   840
cgcattaaag cactccgcct ggggagtacg gtcgcaagac tgaaactcaa aggaattgac   900
```

```
ggggcccgc acaagcggtg gagcatgtgg tttaattcga agcaacgcga agaaccttac    960
caggtcttga catcctctga caatcctaga gataggacgt ccccttcggg ggcagagtga   1020
caggtggtgc atggttgtcg tcagctcgtg tcgtgagatg ttgggttaag tcccgcaacg   1080
agcgcaaccc ttgatcttag ttgccagcat tcagttgggc actctaaggt gactgccggt   1140
gacaaaccgg aggaaggtgg ggatgacgtc aaatcatcat gccccttatg acctgggcta   1200
cacacgtgct acaatggaca gaacaaaggg cagcgaaacc gcgaggttaa gccaatccca   1260
caaatctgtt ctcagttcgg atcgcagtct gcaactcgac tgcgtgaagc tggaatcgct   1320
agtaatcgcg gatcagcatg ccgcggtgaa tacgttcccg ggccttgtac acaccgcccg   1380
tcacaccacg agagtttgta acacccgaag tcggtgaggt aacctttatg gagccagccg   1440
ccgaaggtgg gacagatga                                                1459
```

```
<210> SEQ ID NO 4
<211> LENGTH: 20
<212> TYPE: DNA
<213> ORGANISM: Artificial Sequence
<220> FEATURE:
<223> OTHER INFORMATION: FD1 primer, produced synthetically in
      laboratory

<400> SEQUENCE: 4
agagtttgat cctggctcag                                                 20

<210> SEQ ID NO 5
<211> LENGTH: 17
<212> TYPE: DNA
<213> ORGANISM: Artificial Sequence
<220> FEATURE:
<223> OTHER INFORMATION: RD1 primer, produced synthetically in
      laboratory

<400> SEQUENCE: 5
aaggaggtga tccagcc                                                    17

<210> SEQ ID NO 6
<211> LENGTH: 21
<212> TYPE: DNA
<213> ORGANISM: Artificial Sequence
<220> FEATURE:
<223> OTHER INFORMATION: recAf primer, produced synthetically in
      laboratory

<400> SEQUENCE: 6
gatcgtcarg cagscytwga t                                               21

<210> SEQ ID NO 7
<211> LENGTH: 20
<212> TYPE: DNA
<213> ORGANISM: Artificial Sequence
<220> FEATURE:
<223> OTHER INFORMATION: recAr primer, produced synthetically in
      laboratory

<400> SEQUENCE: 7
ttwccracca taacsccrac                                                 20

<210> SEQ ID NO 8
<211> LENGTH: 560
<212> TYPE: DNA
<213> ORGANISM: Bacillus sp. strain F727 Forward recA Sequence
```

<400> SEQUENCE: 8

```
aacattcggc aaggttccat catgaaactc ggggaaaaga cggatacaag aatttcaaca        60
gttccgagcg gttcccttgc acttgatacc gctctcggaa taggcggata cccgcgcgga       120
cggattattg aagtatacgg acctgaaagc tcaggtaaaa cgactgtagc gcttcatgcg       180
attgctgaag ttcaggagaa aggcggacaa gccgcattta ttgatgctga gcatgccctt       240
gaccctgttt acgcgcaaaa gctcggtgta aatattgagg agctgctgct ttctcagcct       300
gatacgggag agcaggcgct tgagattgcc gaagcgctgg tacgaagcgg agccgtcgat       360
atcgtagttg tcgactctgt tgcggcgctt gtcccgaaag ctgaaatcga aggagacatg       420
ggggattccc acgtcggttt gcaggcccgt ttgatgtctc aagcgctccg taagctttcc       480
ggtgccatca ataaatctaa aacaatcgca atctttatta accaaattcg tgaaaaagtc       540
ggcgttaggg tcggaaaaaa                                                   560
```

<210> SEQ ID NO 9
<211> LENGTH: 567
<212> TYPE: DNA
<213> ORGANISM: Bacillus sp. strain F727 Reverse recA Sequence

<400> SEQUENCE: 9

```
gtataagatt gcgattgttt tagatttatt gatggcaccg gaaagcttac ggagcgcttg        60
agacatcaaa cgggcctgca aaccgacgtg ggaatccccc atgtctcctt cgatttcagc       120
tttcgggaca agcgccgcaa cagagtcgac aactacgata tcgacggctc cgcttcgtac       180
cagcgcttcg gcaatctcaa gcgcctgctc tcccgtatca ggctgagaaa gcagcagctc       240
ctcaatattt acaccgagct tttgcgcgta acagggtca agggcatgct cagcatcaat        300
aaatgcggct tgtccgcctt tctcctgaac ttcagcaatc gcatgaagcg ctacagtcgt       360
tttacctgag ctttcaggtc cgtatacttc aataatccgt ccgcgcgggt atccgcctat       420
tccgagagcg gtatcaagtg caagggaacc gctcggaact gttgaaattc ttgtatccgt       480
cttttccccg agtttcatga tggaaccttt gccgaattgt ttttctattt gcttaagagc       540
catatcwaag rctgwawtra mratcaa                                           567
```

<210> SEQ ID NO 10
<211> LENGTH: 505
<212> TYPE: DNA
<213> ORGANISM: Bacillus sp. strain F727 Consensus recA Sequence

<400> SEQUENCE: 10

```
aaggttccat catgaaactc ggggaaaaga cggatacaag aatttcaaca gttccgagcg        60
gttcccttgc acttgatacc gctctcggaa taggcggata cccgcgcgga cggattattg       120
aagtatacgg acctgaaagc tcaggtaaaa cgactgtagc gcttcatgcg attgctgaag       180
ttcaggagaa aggcggacaa gccgcattta ttgatgctga gcatgccctt gaccctgttt       240
acgcgcaaaa gctcggtgta aatattgagg agctgctgct ttctcagcct gatacgggag       300
agcaggcgct tgagattgcc gaagcgctgg tacgaagcgg agccgtcgat atcgtagttg       360
tcgactctgt tgcggcgctt gtcccgaaag ctgaaatcga aggagacatg ggggattccc       420
acgtcggttt gcaggcccgt ttgatgtctc aagcgctccg taagctttcc ggtgccatca       480
ataaatctaa aacaatcgca atctt                                             505
```

<210> SEQ ID NO 11
<211> LENGTH: 20

```
<212> TYPE: DNA
<213> ORGANISM: Artificial Sequence
<220> FEATURE:
<223> OTHER INFORMATION: phoR-f primer, produced synthetically in
      laboratory

<400> SEQUENCE: 11
ttyarytcat grgavacatt                                              20

<210> SEQ ID NO 12
<211> LENGTH: 20
<212> TYPE: DNA
<213> ORGANISM: Artificial Sequence
<220> FEATURE:
<223> OTHER INFORMATION: phoR-r primer, produced synthetically in
      laboratory
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t

<400> SEQUENCE: 12
ggntayaaan argaggagcc                                              20

<210> SEQ ID NO 13
<211> LENGTH: 998
<212> TYPE: DNA
<213> ORGANISM: Bacillus sp. strain F727 Reverse phoR Sequence

<400> SEQUENCE: 13
tcgttgtctg tatcatattg gttttcagtg ttctcggcct tttcttgcag cagctcattt    60
cttcatccgc caaggaaaga acggagggac agcttgaaaa ggaagccgca tacatagccg   120
gactccttga cgccggccaa gtaaacaata aagaaacga aacggtcatt aaagatgcca    180
gccgtacatt agatatcgac gtgtccgtat taaatgaaaa aggccgcggt ttatatcact   240
caggcagacg cgctgatgac tcggctataa aggaattcgt ctcccgtaat aaaaatgcgg   300
cggcgattca gaacggagag aaagtatggc atggaacggc ccttaaaaac gccgccggcc   360
aaacggcggg atatgtgctc gtttcctcgc ggatcgataa aggttcgaat ataacagggg   420
aaatgtgggg catgctggct gcaagccttt gtactgcttt tattattatc gttttcttct   480
atacgaatat gacctcccgt tacaaaaggt caatcgactc cgcgacaaaa gtggccactg   540
agctgtctaa ggggaactat gacgcccgct cctacggcgg gtacgcaaga cgctcagacc   600
gtctcgggcg cgctatgaac agcctcgctg tggatttgat ggaaatgacg agaacgcagg   660
atatgcagcg cgaccgcctg ctgaccgtca tcgaaaatat cggatcaggt ttgatttaa    720 tagacgggag aggctttatt aatctcgtga acaggtcgta tacgaagcag ttccatacaa   780
atcctgaacg tctgcttcgg cgtctctacc atgacgcatt tgagcatgag gaaatcattc   840
ggctggtcga agacatcttt atgacagaaa cgaagaaacg ccagctgctc acgcttccca   900
tcaaaatcga acggcgctat tttgaggttg acggcgtccc gattatgggc cctgacgatg   960
aatggaaaag gcattgttct cgtgtttcat gatatgac                           998
```